(12) United States Patent
Oku et al.

(10) Patent No.: US 10,653,740 B2
(45) Date of Patent: May 19, 2020

(54) METHOD FOR TREATING FATTY LIVER

(71) Applicants: Amino Up Co., Ltd., Hokkaido (JP); University of the Ryukyus, Okinawa (JP); NPO Amami Functional Foods Study Group, Kagoshima (JP)

(72) Inventors: Hirosuke Oku, Okinawa (JP); Yasuo Kamiyama, Kagoshima (JP); Masashi Inafuku, Okinawa (JP)

(73) Assignees: Amino Up Co., Ltd., Hokkaido (JP); University of the Ryukyus, Okinawa (JP); NPO Amami Functional Foods Study Group, Kagoshima (JP)

(*) Notice: Subject to any disclaimer, the term of this patent is extended or adjusted under 35 U.S.C. 154(b) by 182 days.

(21) Appl. No.: 15/903,823

(22) Filed: Feb. 23, 2018

(65) Prior Publication Data
US 2018/0200317 A1 Jul. 19, 2018

Related U.S. Application Data

(62) Division of application No. 14/911,835, and a division of application No. PCT/JP2014/071397, filed on Aug. 13, 2014.

(30) Foreign Application Priority Data

Aug. 13, 2013 (JP) ................. 2013-168404

(51) Int. Cl.
*A61K 36/00* (2006.01)
*A61K 36/28* (2006.01)
*A23L 33/105* (2016.01)

(52) U.S. Cl.
CPC ............ *A61K 36/28* (2013.01); *A23L 33/105* (2016.08); *A23V 2002/00* (2013.01)

(58) Field of Classification Search
CPC .................................................. A61K 36/00
See application file for complete search history.

(56) References Cited

U.S. PATENT DOCUMENTS

| | | |
|---|---|---|
| 5,698,199 A | 12/1997 | Mori et al. |
| 2011/0165273 A1 | 7/2011 | Guo et al. |

FOREIGN PATENT DOCUMENTS

| | | | |
|---|---|---|---|
| CN | 102754674 A | * | 10/2012 |
| JP | S52-094410 A | | 8/1977 |
| JP | H06-206867 A | | 7/1994 |
| JP | H08-301780 A | | 11/1996 |
| JP | 2000-063259 A | | 2/2000 |
| JP | 2000-212096 A | | 8/2000 |
| JP | 2000-256205 A | | 9/2000 |
| JP | 2001-139485 A | | 5/2001 |
| JP | 3249707 B2 | | 1/2002 |
| JP | 2011-079754 A | | 4/2011 |

OTHER PUBLICATIONS

Noh, Inhibitory effect of a Cirsium setidens extract on hepatic fat accumulation in mice fed a high-fat diet via the induction of fatty acid .beta.-oxidation: Bioscience, biotechnology, and biochemistry, (2013) vol. 77, No. 7, pp. 1424-1429. Electronic Publication Date: Jul. 7, 2013 (Year: 2013).*
Yuichi Kadota "Taxonomy and Distribution of Cirsium brevicaule A. Gray and its Related Species (*Asteraceae*)" Mem. Natn. Sci. Mus., Tokyo (23), 1990.
Liao et al., Biol., Pharm., Bull. 35 (6), 855-860, (2012).
Okinawa Times, Yukan (an evening paper), Jul. 21, 1998 (Jul. 21, 1998), p. 1.
Kiyoshi Sawaguchi et al., "Antimicrobial and Antioxidative Activities of Extracts from the Rhizomes of *Cirsium brevicaule A. Gray* var. *irumtiense Kitam*", Journal of Antibacterial and Antifungal Agents, Japan, 1993, 21(11), 609 to 613 (English abstract is included).
Mori S. et al, Body fat mass reduction and upregulation of uncoupling protein by novel lipolysis-promoting plant extract, International Journal of Biological Sciences, 2009, 5(4), 311-318.
Kim E. and Chung J., Protective effect of Cirsium setidens extract against the alcohol-induced liver injury in rats, FASEB Journal, Apr. 2013, 27(Meeting Abstract Supplement), lb267.
Noh H. et al, Inhibitory effect of a Cirsium setidens extract on hepatic fat accumulation in mice fed a high-fat diet via the induction of fatty acid β-oxidation., Bioscience, Biotechnology, and Biochemistry, Jul. 7, 2013, 77 (7), 1424-1429.
Liao Z. et al, Antidiabetic effect of flavones from Cirsium japonicum DC in diabetic rats., Achives of Pharmacal Research, 2010, 33(3), 353-362.
Naotaka Morita et al., "Flavonoids of Cirsium Plants (*Compositae*) in Japan. (4)", The Japanese Journal of Pharmacognosy, 1964, 18(1), 9 to 11(English abstract is included).
Inafuku M. et al, Cirsium brevicaule A. Gray leaf inhibits adipogenesis in 3T3-LI cells and C57BL/6 mice., Lipids in Health and Disease, Aug. 15, 2013, 12, 124.
Liao Z. et al, Cirsium japonicum flavones enhance adipocyte differentiation and glucose uptake in 3T3-LI cells., Biological & Pharmaceutical Bulletin, 2012, 35(6), 855-860.
Non-final Office Action dated Nov. 24, 2017 by the USPTO for related U.S. Appl. No. 14/911,835.
Restriction Requirement dated Sep. 12, 2017 by the USPTO for related U.S. Appl. No. 14/911,835.

* cited by examiner

Primary Examiner — Qiuwen Mi
(74) Attorney, Agent, or Firm — Hamre, Schumann, Mueller & Larson, P.C.

(57) ABSTRACT

A method of treating fatty liver comprising administering an effective amount of a plant belonging to a genus *Cirsium* to a patient in need of the treatment.

3 Claims, 17 Drawing Sheets
Specification includes a Sequence Listing.

SEQUENCE LISTING

<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: ACTB forward primer

<400> SEQUENCE: 1
cagaaggaga ttactgctct ggct                                           24

<210> SEQ ID NO 2
<211> LENGTH: 19
<212> TYPE: DNA
<213> ORGANISM: Artificial Sequence
<220> FEATURE:
<223> OTHER INFORMATION: ACTB reverse primer

<400> SEQUENCE: 2
ggagccaccg atccacaca                                                 19

<210> SEQ ID NO 3
<211> LENGTH: 24
<212> TYPE: DNA
<213> ORGANISM: Artificial Sequence
<220> FEATURE:
<223> OTHER INFORMATION: Peg/Mest forward primer

<400> SEQUENCE: 3 gttttttcacc tacaaaggcc tacg                                          24

<210> SEQ ID NO 4
<211> LENGTH: 24
<212> TYPE: DNA
<213> ORGANISM: Artificial Sequence
<220> FEATURE:
<223> OTHER INFORMATION: Peg/Mest reverse primer

<400> SEQUENCE: 4
cacaccgaca gaatcttggt agaa                                           24

<210> SEQ ID NO 5
<211> LENGTH: 23
<212> TYPE: DNA
<213> ORGANISM: Artificial Sequence
<220> FEATURE:
<223> OTHER INFORMATION: PPAR gamma forward primer

<400> SEQUENCE: 5
aggccgagaa ggagaagctg ttg                                            23

<210> SEQ ID NO 6
<211> LENGTH: 22
<212> TYPE: DNA
<213> ORGANISM: Artificial Sequence
<220> FEATURE:
<223> OTHER INFORMATION: PPAR gamma reverse primer

<400> SEQUENCE: 6
tggccacctc tttgctgtgc tc                                             22

<210> SEQ ID NO 7
<211> LENGTH: 20
<212> TYPE: DNA
<213> ORGANISM: Artificial Sequence -continued

```
<220> FEATURE:
<223> OTHER INFORMATION: FABP4 forward primer

<400> SEQUENCE: 7
agcatcataa ccctagatgg                                              20

<210> SEQ ID NO 8
<211> LENGTH: 22
<212> TYPE: DNA
<213> ORGANISM: Artificial Sequence
<220> FEATURE:
<223> OTHER INFORMATION: FABP4 reverse primer

<400> SEQUENCE: 8
cataacacat tccaccacca gc                                           22

<210> SEQ ID NO 9
<211> LENGTH: 20
<212> TYPE: DNA
<213> ORGANISM: Artificial Sequence
<220> FEATURE:
<223> OTHER INFORMATION: SREBP-1c forward primer

<400> SEQUENCE: 9
ggagccatgg attgcacatt                                              20

<210> SEQ ID NO 10
<211> LENGTH: 20
<212> TYPE: DNA
<213> ORGANISM: Artificial Sequence
<220> FEATURE:
<223> OTHER INFORMATION: SREBP-1c reverse primer

<400> SEQUENCE: 10
gcttccagag aggaggccag                                              20

<210> SEQ ID NO 11
<211> LENGTH: 20
<212> TYPE: DNA
<213> ORGANISM: Artificial Sequence
<220> FEATURE:
<223> OTHER INFORMATION: LPL forward primer

<400> SEQUENCE: 11
agggctctgc ctgagttgta                                              20

<210> SEQ ID NO 12
<211> LENGTH: 20
<212> TYPE: DNA
<213> ORGANISM: Artificial Sequence
<220> FEATURE:
<223> OTHER INFORMATION: LPL reverse primer

<400> SEQUENCE: 12
agaaatctcg aaggcctggt                                              20

<210> SEQ ID NO 13
<211> LENGTH: 22
<212> TYPE: DNA
<213> ORGANISM: Artificial Sequence
<220> FEATURE:
<223> OTHER INFORMATION: RORC forward primer

<400> SEQUENCE: 13
tcctgccacc ttgagtatag tc                                           22
```

<210> SEQ ID NO 14
<211> LENGTH: 21
<212> TYPE: DNA
<213> ORGANISM: Artificial Sequence
<220> FEATURE:
<223> OTHER INFORMATION: RORC reverse primer

<400> SEQUENCE: 14
gtaagttggc cgtcagtgct a                                              21

<210> SEQ ID NO 15
<211> LENGTH: 20
<212> TYPE: DNA
<213> ORGANISM: Artificial Sequence
<220> FEATURE:
<223> OTHER INFORMATION: IRS-1 forward primer

<400> SEQUENCE: 15
ccagagtcaa gcctcacaca                                                20

<210> SEQ ID NO 16
<211> LENGTH: 20
<212> TYPE: DNA
<213> ORGANISM: Artificial Sequence
<220> FEATURE:
<223> OTHER INFORMATION: IRS-1 reverse primer

<400> SEQUENCE: 16
gaagactgct gctgctgttg                                                20

<210> SEQ ID NO 17
<211> LENGTH: 17
<212> TYPE: DNA
<213> ORGANISM: Artificial Sequence
<220> FEATURE:
<223> OTHER INFORMATION: FAS forward primer

<400> SEQUENCE: 17
tgctcccagc tgcaggc                                                   17

<210> SEQ ID NO 18
<211> LENGTH: 20
<212> TYPE: DNA
<213> ORGANISM: Artificial Sequence
<220> FEATURE:
<223> OTHER INFORMATION: FAS reverse primer

<400> SEQUENCE: 18
gcccggtagc tctgggtgta                                                20

<210> SEQ ID NO 19
<211> LENGTH: 20
<212> TYPE: DNA
<213> ORGANISM: Artificial Sequence
<220> FEATURE:
<223> OTHER INFORMATION: FXR alpha forward primer

<400> SEQUENCE: 19
ccctgcttga tgtgctacaa                                                20

<210> SEQ ID NO 20
<211> LENGTH: 19
<212> TYPE: DNA
<213> ORGANISM: Artificial Sequence
<220> FEATURE:
<223> OTHER INFORMATION: FXR alpha reverse primer

```
<400> SEQUENCE: 20
gtgtccatca ctgcacatc                                              19

<210> SEQ ID NO 21
<211> LENGTH: 23
<212> TYPE: DNA
<213> ORGANISM: Artificial Sequence
<220> FEATURE:
<223> OTHER INFORMATION: C/EBP alpha forward primer

<400> SEQUENCE: 21
tggacaagaa cagcaacgag tac                                         23

<210> SEQ ID NO 22
<211> LENGTH: 21
<212> TYPE: DNA
<213> ORGANISM: Artificial Sequence
<220> FEATURE:
<223> OTHER INFORMATION: C/EBP alpha reverse primer

<400> SEQUENCE: 22
gcagttgccc atggccttga c                                           21

<210> SEQ ID NO 23
<211> LENGTH: 20
<212> TYPE: DNA
<213> ORGANISM: Artificial Sequence
<220> FEATURE:
<223> OTHER INFORMATION: GLUT4 forward primer

<400> SEQUENCE: 23
ctgcaaagcg taggtaccaa                                             20

<210> SEQ ID NO 24
<211> LENGTH: 17
<212> TYPE: DNA
<213> ORGANISM: Artificial Sequence
<220> FEATURE:
<223> OTHER INFORMATION: GLUT4 reverse primer

<400> SEQUENCE: 24
cctcccgccc ttagttg                                                17

<210> SEQ ID NO 25
<211> LENGTH: 20
<212> TYPE: DNA
<213> ORGANISM: Artificial Sequence
<220> FEATURE:
<223> OTHER INFORMATION: 18S rRNA forward primer

<400> SEQUENCE: 25
cggacaggat tgacagattg                                             20

<210> SEQ ID NO 26
<211> LENGTH: 20
<212> TYPE: DNA
<213> ORGANISM: Artificial Sequence
<220> FEATURE:
<223> OTHER INFORMATION: 18S rRNA reverse primer

<400> SEQUENCE: 26
caaatcgctc caccaactaa                                             20

<210> SEQ ID NO 27
```

```
<211> LENGTH: 22
<212> TYPE: DNA
<213> ORGANISM: Artificial Sequence
<220> FEATURE:
<223> OTHER INFORMATION: PPAR alpha forward primer

<400> SEQUENCE: 27
cctcagggta ccactacgga gt                                          22

<210> SEQ ID NO 28
<211> LENGTH: 18
<212> TYPE: DNA
<213> ORGANISM: Artificial Sequence
<220> FEATURE:
<223> OTHER INFORMATION: PPAR alpha reverse primer

<400> SEQUENCE: 28
gccgaatagt tcgccgaa                                               18

<210> SEQ ID NO 29
<211> LENGTH: 21
<212> TYPE: DNA
<213> ORGANISM: Artificial Sequence
<220> FEATURE:
<223> OTHER INFORMATION: CPT1b forward primer

<400> SEQUENCE: 29
ccaaacgtca ctgcctaagc t                                           21

<210> SEQ ID NO 30
<211> LENGTH: 20
<212> TYPE: DNA
<213> ORGANISM: Artificial Sequence
<220> FEATURE:
<223> OTHER INFORMATION: CPT1b reverse primer

<400> SEQUENCE: 30
ggccgcacag aatccaagta                                             20

<210> SEQ ID NO 31
<211> LENGTH: 23
<212> TYPE: DNA
<213> ORGANISM: Artificial Sequence
<220> FEATURE:
<223> OTHER INFORMATION: CPT1a forward primer

<400> SEQUENCE: 31
aaagatcaat cggaccctag aca                                         23

<210> SEQ ID NO 32
<211> LENGTH: 20
<212> TYPE: DNA
<213> ORGANISM: Artificial Sequence
<220> FEATURE:
<223> OTHER INFORMATION: CPT1a reverse primer

<400> SEQUENCE: 32
cagcgagtag cgcatagtca                                             20

<210> SEQ ID NO 33
<211> LENGTH: 19
<212> TYPE: DNA
<213> ORGANISM: Artificial Sequence
<220> FEATURE:
<223> OTHER INFORMATION: FAS sense primer

<400> SEQUENCE: 33
```

```
tcgtgggcta cagcatggt                                                     19

<210> SEQ ID NO 34
<211> LENGTH: 20
<212> TYPE: DNA
<213> ORGANISM: Artificial Sequence
<220> FEATURE:
<223> OTHER INFORMATION: FAS anti sense primer

<400> SEQUENCE: 34
gccctctgaa gtcgaagaag                                                    20

<210> SEQ ID NO 35
<211> LENGTH: 15
<212> TYPE: DNA
<213> ORGANISM: Artificial Sequence
<220> FEATURE:
<223> OTHER INFORMATION: ACTB sense primer

<400> SEQUENCE: 35
tcaccgagcg cggct                                                         15

<210> SEQ ID NO 36
<211> LENGTH: 21
<212> TYPE: DNA
<213> ORGANISM: Artificial Sequence
<220> FEATURE:
<223> OTHER INFORMATION: ACTB anti sense primer

<400> SEQUENCE: 36
taatgtcacg cacgatttcc c                                                  21
```

METHOD FOR TREATING FATTY LIVER

CROSS REFERENCE TO RELATED APPLICATIONS

This application is a divisional of U.S. patent application Ser. No. 14/911,835, which entered U.S. national phase on Feb. 12, 2016 from international patent application No. PCT/JP2014/071397, which was filed on Aug. 13, 2014, which claimed priority from Japan Patent Application No. 2013-168404 filed on Aug. 13, 2013, the entire content of which is herein incorporated as reference.

SEQUENCE LISTING

The instant application contains a Sequence Listing which has been submitted electronically in ASCII format and is hereby incorporated by reference in its entirety. Said ASCII copy, created on Mar. 17, 2016, is named 14F079-PCT_Revised SEQUENCE LISTING.txt and is 7,297 bytes in size.

BACKGROUND OF THE INVENTION

1. Field of the Invention

The present disclosure relates to a method for treating fatty liver.

2. Description of the Related Art

Thistles are plants belonging to the genus *Cirsium* of the family Asteraceae, and are distributed over wide areas from mountainous districts to seabeaches. In the world, there are 250 species or more of thistles, which are widely distributed over the Northern Hemisphere. Very wide local variations occur in the thistles. It is considered that there are 100 species or more of thistles in Japan, in which a new species of thistles may be currently discovered. In addition, there are also interspecific hybrids, and therefore, it is considered that taxonomy of the thistles may be difficult.

It has been made clear that the *Cirsium brevicaule* group in the thistle includes four species of *Cirsium brevicaule* A. Gray, *C. boninense*, *C. spinosum*, and *C. maritimum*, and it has been reported that the four species are distributed from the Pacific coast south of the Kanto to the Ryukyu Islands in Japan, as well as over part of Taiwan (Non-Patent Literature 1).

Plants belonging to the genus *Cirsium* have been reported to have various pharmacological actions. Patent Literature 1 discloses an antibacterial agent and an antioxidant, comprising, as an active ingredient, an extract from the rhizome of *Cirsium brevicaule* A. Gray. Patent Literature 2 discloses that *C. maritimum* Makino has a blood glucose elevation inhibitory action, and Patent Literature 3 discloses that *C. maritimum* Makino has antimutagenicity. Patent Literature 4 discloses that *C. japonicum* has a ceramide production promoting action and can be used as a moisturizer. Non-Patent Literature 2 reports that a plant belonging to the genus *Cirsium*, grown in Japan, has the action of promoting differentiation of fat cells from mouse fibroblasts (3T3-L1 cells). Patent Literature 5 discloses that plants belonging to the genus *Cirsium* (*Cephalonoplos segetum* (Bieb.) Kitam. and *Cirsium japonicum* DC.) have a lipolysis promoting action.

CITATION LIST

Patent Literature

Patent Literature 1: Unexamined Japanese Patent Application Kokai Publication No. H6-206867;
Patent Literature 2: Unexamined Japanese Patent Application Kokai Publication No. 2000-212096;
Patent Literature 3: Unexamined Japanese Patent Application Kokai Publication No. 2000-256205;
Patent Literature 4: Unexamined Japanese Patent Application Kokai Publication No. 2011-79754;
Patent Literature 5: Unexamined Japanese Patent Application Kokai Publication No. H8-301780;

Non-Patent Literature

Non-Patent Literature 1: Yuichi Kadota "Taxonomy and Distribution of *Cirsium brevicaule* A. GRAY and its Related Species (Asteraceae)" Mem. Natn. Sci. Mus., Tokyo (23), 1990;
Non-Patent Literature 2: Liao et al., Biol., Pharm., Bull. 35 (6), 855-860, (2012).

SUMMARY OF THE INVENTION

Until now, however, any plants belonging to the genus *Cirsium* have not been reported to have a fat accumulation inhibitory action.

The present inventors newly found that a plant belonging to the genus *Cirsium* has an excellent fat accumulation inhibitory action, and the present disclosure was thus accomplished. An objective of the present disclosure is to provide a fat accumulation inhibitor having an excellent effect, a drug including the fat accumulation inhibitor, a prophylactic or therapeutic agent for fatty liver, a food or drink, and a method for producing a fat accumulation inhibitor.

In order to achieve the above-described objective, a fat accumulation inhibitor according to a first aspect of the present disclosure includes, as an active ingredient, a plant belonging to the genus *Cirsium*.

The plant belonging to the genus *Cirsium* may be *Cirsium brevicaule* A. Gray.

A drug according to a second aspect of the present disclosure includes,
as an active ingredient, the fat accumulation inhibitor according to the first aspect of the present disclosure.

A prophylactic or therapeutic agent for fatty liver according to a third aspect of the present disclosure includes, as an active ingredient, the fat accumulation inhibitor according to the first aspect of the present disclosure.

A food or drink according to a fourth aspect of the present disclosure includes, the fat accumulation inhibitor according to the first aspect of the present disclosure.

A method for producing a fat accumulation inhibitor according to a fifth aspect of the present disclosure includes a step of performing an extraction operation on a plant belonging to the genus *Cirsium* using a solvent, to obtain an extraction liquid.

A fat accumulation inhibitor according to a sixth aspect of the present disclosure is obtained by the method for producing of a fat accumulation inhibitor according to the fifth aspect of the present disclosure.

In accordance with the present disclosure, there can be provided a fat accumulation inhibitor having an excellent effect, a drug comprising the fat accumulation inhibitor, a prophylactic or therapeutic agent for fatty liver, a food or drink, and a method for producing a fat accumulation inhibitor.

DETAILED DESCRIPTION OF THE PRESENTLY PREFERRED EMBODIMENTS

Figure 1A:
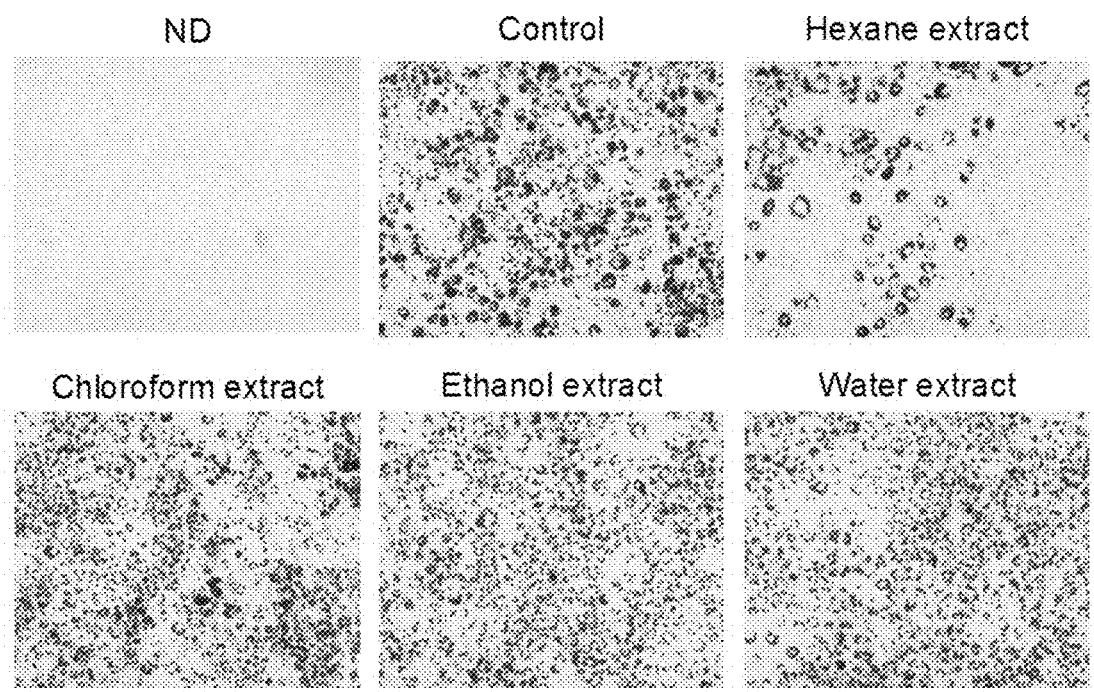
FIG. 1A is a view showing the formation of fat droplets.

Embodiments of the present disclosure will be described in detail below.

First, a fat accumulation inhibitor according to the present disclosure will be described in detail. The fat accumulation inhibitor according to the present disclosure comprises, as an active ingredient, a plant belonging to the genus *Cirsium*.

Examples of the plant belonging to the genus *Cirsium* used in the present disclosure include *Cirsium brevicaule* A. Gray, *C. boninense*, *C. spinosum*, *C. maritimum*, and the like, belonging to the genus *Cirsium* of the family Asteraceae (excluding *Cephalonoplos segetum* (Bieb.) Kitam. and *Cirsium japonicum* DC.). Of these, *Cirsium brevicaule* A. Gray is most preferably used. Any plants belonging to the genus *Cirsium*, exerting the effects of the present disclosure, can be selected as appropriate.

In the present disclosure, plants belonging to the genus *Cirsium*, grown for optional days, can be used. Further, the leaves, stems, roots, rhizomes, fruits, seeds, seed coats, flowers, and the like of the plants belonging to the genus *Cirsium* can be used, and the leaves of the plants belonging to the genus *Cirsium* can be preferably used.

In the present disclosure, the plant belonging to the genus *Cirsium*, prepared in a crude form or a form such as a dry powder (for example, prepared by powdering a lyophilized plant belonging to the genus *Cirsium* in a mortar or the like), a squeezed juice, or an extract from a plant belonging to the genus *Cirsium* (described later), is used. A commercially available extract of a plant belonging to the genus *Cirsium*, a powder of a plant belonging to the genus *Cirsium*, or the like may be used. Thus, as used herein, "plant belonging to the genus *Cirsium*" contained in the fat accumulation inhibitor according to the present disclosure refers to a plant belonging to the genus *Cirsium* in a crude state, a dry powder of a plant belonging to the genus *Cirsium*, a squeezed juice of a plant belonging to the genus *Cirsium*, an extract from a plant belonging to the genus *Cirsium* (described later), an extract of a plant belonging to the genus *Cirsium*, or the like.

The fat accumulation inhibitor according to the present disclosure has the effect of inhibiting accumulation of fat in a fat cell to reduce the expression of a fatty acid synthase (FAS).

Next, a method for producing a fat accumulation inhibitor according to the present disclosure will be described in detail.

The method for producing a fat accumulation inhibitor according to the present disclosure comprises a step of performing an extraction operation on a plant belonging to the genus *Cirsium* using a solvent, to obtain an extraction liquid.

Examples of the plant belonging to the genus *Cirsium* used in the step include plants belonging to the genus *Cirsium* in a crude state, the dry powders of plants belonging to the genus *Cirsium*, and the like. The kinds of the plants belonging to the genus *Cirsium*, days for which the plants are grown, and the sites used of the plants are the same as described above.

The above-described phrase "performing extraction operation on plant belonging to genus *Cirsium* using solvent, to obtain extraction liquid" refers to, for example, immersing a plant belonging to the genus *Cirsium* in a solvent (for example, immersing the plant for two hours at 37° C.), to obtain an extraction liquid; immersing a plant belonging to the genus *Cirsium* in a solvent, then separating the solvent (for example, filtering the solvent under reduced pressure), and washing the residue with the solvent, to obtain an extraction liquid; or immersing a plant belonging to the genus *Cirsium* in a solvent, then separating the solvent, washing the residue with the solvent, and further repeating the separation of the solvent and the washing of the residue with the solvent once or more, to obtain an extraction liquid. Thus, "extraction operation" as used herein represents immersing a plant belonging to the genus *Cirsium* in a solvent; separating the solvent; washing the residue with the solvent; and/or the like. As used herein, "extraction liquid" represents a liquid obtained by immersing a plant belonging to the genus *Cirsium* in a solvent; a liquid obtained by immersing a plant belonging to the genus *Cirsium* in a solvent, then separating the solvent, and washing the residue with the solvent; or the like.

Examples of the above-described term "solvent" include water, hot water (for example, at 50° C. or more), alcohols, hexane, chloroform, ethers, esters, and ketones. The alcohols are, for example, lower alcohols such as ethanol, methanol, n-propanol, isopropanol, and n-butanol, and polyhydric alcohols such as 1,3-butylene glycol, propylene glycol, and glycerol; the ethers are, for example, diethyl ether, propyl ether, and the like; the esters are, for example, butyl acetate, ethyl acetate, and the like; and the ketones are, for example, acetone, ethyl methyl ketone, and the like. A mixed solvent in which two or more of the solvents are combined may also be used. It is also acceptable to perform an extraction operation in which different solvents are used in combination in turn, such as, for example, an extraction operation using hexane, followed by an extraction operation on the resulting residue using chloroform. As such a solvent, water, hot water, ethanol, and/or the like are preferably used in consideration of the influence of the solvent on a human body.

In the present specification, an extract obtained by the step of performing an extraction operation on a plant belonging to the genus *Cirsium* using a solvent, to obtain an extraction liquid, may be referred to as "extract from plant belonging to the genus *Cirsium*"; an extract obtained by the step of performing an extraction operation on *Cirsium brevicaule* A. Gray using a solvent, to obtain an extraction liquid, may be referred to as "*Cirsium brevicaule* A. Gray extract"; an extract obtained by the step of performing an extraction operation on a plant belonging to the genus *Cirsium* using hexane as a solvent, to obtain an extraction liquid, may be referred to as "hexane extract"; an extract obtained by the step of performing an extraction operation on a plant belonging to the genus *Cirsium* using chloroform as a solvent, to obtain an extraction liquid, may be referred to as "chloroform extract"; and an extract obtained by the step of performing an extraction operation on a plant belonging to the genus *Cirsium* using ethanol as a solvent, to obtain an extraction liquid, may be referred to as "ethanol extract".

The fat accumulation inhibitor according to the present specification described above may also be obtained by the production method described above. In other words, the above-described "extract from plant belonging to the genus *Cirsium*" can be used as the fat accumulation inhibitor because of having the effect of inhibiting accumulation of fat in a fat cell to reduce the expression of a fatty acid synthase (FAS). For example, a specific fraction obtained by further subjecting an extract obtained with a specific solvent to solid-phase extraction and/or the like may be used as the fat accumulation inhibitor, or specific Fraction obtained by further subjecting the specific fraction obtained by the solid-phase extraction to HPLC and/or the like may be used as the fat accumulation inhibitor.

Next, a drug and a food or drink according to the present disclosure will be described in detail.

The fat accumulation inhibitor according to the present disclosure can be used in the drug. The drug according to the present disclosure comprises the above-described fat accumulation inhibitor as an active ingredient.

A method for administering the drug according to the present disclosure can be selected as appropriate from oral administration, intravenous administration, intraperitoneal administration, intradermal administration, sublingual administration, and the like. The dosage form of the drug may be optional, and the drug can be prepared as appropriate in, for example, an oral solid preparation such as a tablet, a granule, a powder, or a capsule; an oral liquid preparation such as an internal liquid medicine or a syrup; a parenteral liquid preparation such as an injection; or the like.

Further, the drug according to the present disclosure may contain, as appropriate, an excipient, a binder, a disintegrant, a thickener, a dispersant, a reabsorption promoter, a corrigent, a buffer, a surfactant, a solubilizer, a preservative, an emulsifier, an isotonizing agent, a stabilizer, a pH adjustor, and/or the like which are usually used. Further, the drug according to the present disclosure may contain, as appropriate, another active ingredient (for example, fatty liver inhibitor) except the above-described fat accumulation inhibitor.

The dosage of the fat accumulation inhibitor which is the active ingredient of the drug according to the present disclosure can be set as appropriate depending on the age, body weight, indication, and/or the like of a patient. All of administration during a meal, postprandial administration, preprandial administration, administration between meals, administration at bedtime, and the like are possible.

The drug according to the present disclosure comprises, as an active ingredient, the fat accumulation inhibitor according to the present disclosure, and therefore exerts the action of inhibiting accumulation of fat in a fat cell and particularly improving fat metabolism in the liver, in turn, to inhibit fatty liver, to reduce subcutaneous fat, to inhibit and prevent obesity, to improve the protection against a tendency to obesity, and the like. In particular, the present disclosure offers an excellent fat accumulation inhibitory action in the liver, and can therefore provide a prophylactic or therapeutic agent for fatty liver. The present inventors found that one mechanism of the fat accumulation inhibitory effect is caused not by a lipolysis promotion action but by reduction of the expression of a fatty acid synthase (FAS) (described in Examples later), and the present disclosure was thus accomplished. In recent years, it has been suggested that fatty liver particularly has not only a relationship with development of cirrhosis or liver cancer but also the likelihoods of the increased risk of developing diabetes and the promotion of arteriosclerosis. Therefore, it is particularly important that the drug according to the present disclosure (prophylactic or therapeutic agent for fatty liver) can inhibit accumulation of fat in the liver and can inhibit fatty liver.

Further, the fat accumulation inhibitor according to the present disclosure can be used in a food or drink. The food or drink according to the present disclosure comprises the above-described fat accumulation inhibitor.

The food or drink according to the present disclosure can be prepared in a granular, granulous, paste, gel, solid, or liquid form, or the like. Further, an excipient, a binder, a disintegrant, a thickener, a dispersant, a reabsorption promoter, a corrigent, a buffer, a surfactant, a solubilizer, a preservative, an emulsifier, an isotonizing agent, a stabilizer, a pH adjustor, and/or the like which are permitted to be contained in foods or drinks can be contained as appropriate. Further, application to foods or drinks, functional foods, foods for sick people, foods for specified health uses, and the like which are based on the concept of fatty liver inhibition and/or the like and show the information of the concept as needed is possible. Further, the fat accumulation inhibitor according to the present disclosure can be used in feed for mammals and the like, pet foods, supplements for pets, and the like, as well as foods or drinks.

EXAMPLES

The present disclosure will be specifically described below with reference to examples. However, the present disclosure is not limited to the examples.

Example 1

A *Cirsium brevicaule* A. Gray extract was prepared from a *Cirsium brevicaule* A. Gray leaf and was subjected to a cultured cell experiment.

(Preparation of *Cirsium brevicaule* A. Gray Extract)

The *Cirsium brevicaule* A. Gray leaf was washed with water and then sterilized with hypochlorous acid. Then, the leaf was sufficiently dewatered, and was pre-frozen. Then, the *Cirsium brevicaule* A. Gray leaf was lyophilized using a vacuum drying apparatus (Marui & Co., Ltd.). The lyophilized leaf was ground by a grinding machine and was sieved to remove non-powdered products and to obtain the lyophilized powder of the *Cirsium brevicaule* A. Gray leaf Extraction treatment was carried out by adding 10 mL of hexane to 1 g of the lyophilized powder and by immersing the lyophilized powder in the hexane at 37° C. for 2 hours. After the extraction, an extraction liquid was separated by filtration under reduced pressure, and the residue was washed twice with 10 mL of hexane. The liquid generated by the washing was mixed into the extraction liquid obtained in advance, to make a hexane extract.

The residue obtained after the washing with the hexane in advance was allowed to be under reduced pressure, to thereby remove the remaining hexane. Extraction treatment was carried out by adding 10 mL of chloroform to the residue obtained after the removal of the hexane and by immersing the residue in the chloroform at 37° C. for 2 hours. After the extraction, an extraction liquid was separated by filtration under reduced pressure, and the residue was washed twice with 10 mL of chloroform. The liquid generated by the washing was mixed into the extraction liquid obtained in advance, to make a chloroform extract.

The residue obtained after the washing with the chloroform in advance was allowed to be under reduced pressure, to thereby remove the remaining chloroform. Extraction treatment was carried out by adding 10 mL of ethanol to the residue obtained after the removal of the chloroform and by immersing the residue in the ethanol at 37° C. for 2 hours. After the extraction, an extraction liquid was separated by filtration under reduced pressure, and the residue was washed twice with 10 mL of ethanol. The liquid generated by the washing was mixed into the extraction liquid obtained in advance, to make an ethanol extract.

The residue obtained after the washing with the ethanol in advance was allowed to be under reduced pressure, to thereby remove the remaining ethanol. Extraction treatment was carried out by adding 10 mL of distilled water to the residue obtained after the removal of the ethanol and by immersing the residue in the distilled water at 37° C. for 2 hours. After the extraction, an extraction liquid was separated by filtration under reduced pressure, and the residue was washed twice with 10 mL of distilled water. The liquid generated by the washing was mixed into the extraction liquid obtained in advance, to make a water extract.

The hexane extract, chloroform extract, and ethanol extract obtained by the above preparation method were dried and solidified under reduced pressure, and the water extract was lyophilized. Each extract was dissolved in dimethyl sulfoxide, to obtain 25 mg/mL of each solution.

(Culture of Mouse Fibroblasts (3T3-L1 Cells))

Mouse fibroblasts (3T3-L1 cells) were seeded in 24-well plates in Dulbecco/Vogt modified Eagle's minimum essential medium (DMEM) supplemented with 10% of bovine serum to satisfy $5 \times 10^3$ cells/mL/well. In an incubator (37° C., 5% $CO_2$), the cells were cultured until reaching confluence while replacing the medium every other day. After reaching the confluence, the cells were further cultured for 2 days, followed by initiating induction of differentiation of the cells.

(Induction of Differentiation of 3T3-L1 Cells into Fat Cells)

The differentiation of the 3T3-L1 cells into fat cells was induced by culturing the cells for 2 days in DMEM mixed with 10% fetal bovine serum (FBS), 50 nM isobutylmethylxanthine (IBMX), 1 µM dexamethasone (DEX), and 10 µg/mL insulin. Two days after the initiation of the differentiation induction, the medium was replaced with DMEM mixed with 10% FBS and 10 µg/mL insulin. Two days after the replacement, the medium was replaced, and the cells were cultured until four days thereafter. Each *Cirsium brevicaule* A. Gray extract obtained as described above was added to the medium from the initiation of the induction of the differentiation of the 3T3-L1 cells to the end of the experiment so that the extract had a final concentration of 50 µg/mL.

(Oil Red O Staining of 3T3-L1 Cells Differentiation-Induced into Fat Cells, and Measurement of Intracellular Neutral Fat (Triglyceride: TG) Level)

The lipid accumulation inhibitory effect of each extract from the *Cirsium brevicaule* A. Gray leaf was evaluated by evaluating the number of fat droplets formed in the 3T3-L1 cells differentiation-induced into the fat cells after the end of the culture (hereinafter referred to as "cultured fat cells"), and an intracellular neutral fat (triglyceride: TG) level.

The cultured fat cells were washed with phosphate buffered saline (PBS) and formalin-fixed. The fixed cells were re-washed with PBS, and then immersed in 60% isopropanol for 1 minute. Then, fat droplets were stained, for 10 minutes, with Oil Red O (Wako Pure Chemical Industries, Ltd.) dissolved in 60% isopropanol (for an experiment technique using oil red O, reference was made to "Method for Researching Food Functions" (Kohrin) pp. 133-136). Then, the cells were washed once with 60% isopropanol and washed twice with PBS, and the formation of the fat droplets in the cells was evaluated by visual observation under an optical microscope.

The cultured fat cells obtained after the culture of the cells to which the hexane extract had been added were washed with PBS and lysed in 0.1% sodium lauryl sulfate, and lipids were extracted from the cell lysate. For the extraction, the method of Bligh & Dyer (Bligh E G and Dyer W J, A rapid method of total lipid extraction and purification, Canadian Journal of Biochemistry and Physiology 1959; 37 (8):

911-917) was used. The extracted lipids were dissolved in isopropanol containing 10% of Triton X-100, and a neutral fat (triglyceride: TG) level was measured using Triglyceride E-test WAKO (manufactured by Wako Pure Chemical Industries, Ltd.). The value of the TG level was corrected with the concentration of protein in the cell lysate (measured using Qubit Fluorometer (Invitrogen)), and the corrected value was regarded as an intracellular neutral fat (triglyceride: TG) level. As a testing method, the Student's t-test was used to detect the significant difference between two groups.

(Results)

Figure 1B:
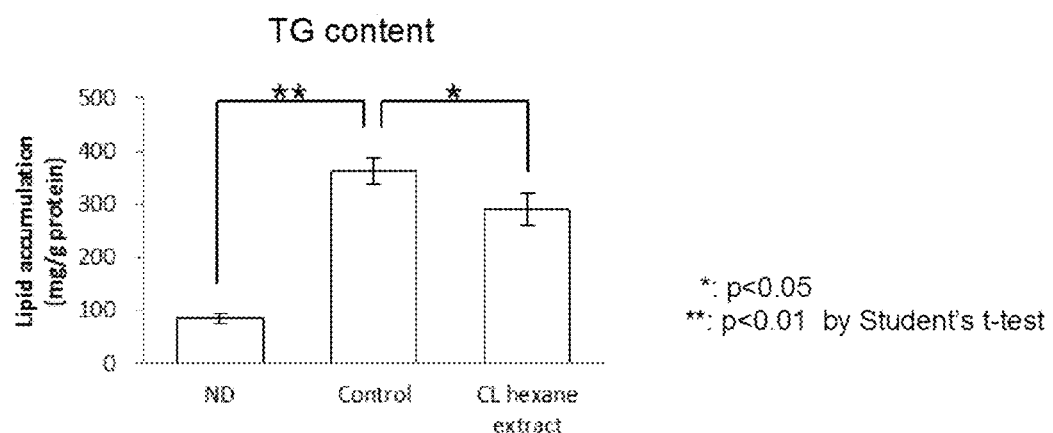
FIG. 1B is a view showing the results of measurement of an intracellular neutral fat (triglyceride: TG) level.

The results of the Oil Red O staining are shown in FIG. 1A, and the results of the measurement of the intracellular neutral fat (triglyceride: TG) level are shown in FIG. 1B. In FIGS. 1A and 1B, "ND" shows 3T3-L1 cells that were not subjected to differentiation induction treatment (Non-Differentiation, ND), and "CONTROL" shows cells obtained by subjecting the cells to differentiation induction treatment, adding dimethyl sulfoxide to the cells, and culturing the cells. It was shown that the number of fat droplets formed in the cells obtained by adding the hexane extract of the *Cirsium brevicaule* A. Gray leaf to the cells and culturing the cells was obviously less than that in each of the chloroform extract, the ethanol extract, and the water extract (FIG. 1A).

differentiation of the 3T3-L1 cells to the end of the experiment so that the extract had a final concentration of 50 µg/mL.

The cultured fat cells were washed with PBS, and 800 µL of TRIzol reagent (Ambion) was added to the cells to obtain a cell lysate. The cell lysate was mixed with 200 µL of chloroform and left standing at room temperature for 5 minutes, followed by separating the cell lysate into two layers by centrifugation at 12,000×g for 15 minutes. The collected upper layer (water layer) was mixed with an equivalent amount of 70% ethanol, to purify total RNA using Pure Link RNA Mini Kit (Ambion). Using High Capacity RNA-to-cDNA Kit (Applied Biosystems), cDNA was synthesized from 2 µg of total RNA.

Fast SYBR Green Master Mix (Applied Biosystems) and a primer for sensing gene expression of interest (Table 1) were added to the synthesized cDNA as a template, and gene expression analysis was carried out by StepOne Real-Time PCR System (Applied Biosystems). Each gene expression data was corrected with the expression level of housekeeping gene (β-actin, ACTB) as an internal standard, and the variations of the lipolysis promotion-related genes and the lipogenesis-related genes (Table 1) with each *Cirsium brevicaule* A. Gray extract were analyzed.

TABLE 1

| Gene name | | Forward primer | Reverse primer |
|---|---|---|---|
| ACTB (internal standard) | — | SEQ ID NO: 1 | SEQ ID NO: 2 |
| Peg/Mest | Patemally expressed/Mesoderm specific transcript | SEQ ID NO: 3 | SEQ ID NO: 4 |
| PPAR γ | Peroxisome Proliferator-Activated Receptor γ | SEQ ID NO: 5 | SEQ ID NO: 6 |
| FABP4 | Fatty acid binding protein 4 | SEQ ID NO: 7 | SEQ ID NO: 8 |
| SREBP-1c | Sterol regulatory element-binding protein-1c | SEQ ID NO: 9 | SEQ ID NO: 10 |
| LPL | Lip oprotein lipase | SEQ ID NO: 11 | SEQ ID NO: 12 |
| RORC | RAR-related orphan receptor gamma | SEQ ID NO: 13 | SEQ ID NO: 14 |
| IRS-1 | Insulin receptor substrate 1 | SEQ ID NO: 15 | SEQ ID NO: 16 |
| FAS | Fatty acid synthase (FAS) | SEQ ID NO: 17 | SEQ ID NO: 18 |
| FXR α | Farnesoid X receptor alpha | SEQ ID NO: 19 | SEQ ID NO: 20 |
| C/EBP α | CCAAT-enhancer-binding proteins α | SEQ ID NO: 21 | SEQ ID NO: 22 |
| GLUT4 | Glucose transporter type 4 | SEQ ID NO: 23 | SEQ ID NO: 24 |

In addition, it was shown that the intracellular neutral fat (triglyceride: TG) level in the cells obtained by adding the hexane extract of the *Cirsium brevicaule* A. Gray leaf to the cells and culturing the cells was significantly lower than that in the control (FIG. 1B).

Based on the above, it was shown that the extract of the *Cirsium brevicaule* A. Gray leaf according to the present example inhibited the accumulation of lipids in the cultured fat cells.

(Influence on Expression of Lipolysis Promotion-Related Genes and Lipogenesis-Related Genes)

The influence of the hexane extract of the *Cirsium brevicaule* A. Gray leaf on the expression of the lipolysis promotion-related genes and lipogenesis-related genes (Table 1) of the cultured fat cells was examined.

The differentiation of the 3T3-L1 cells into fat cells was induced by culturing the cells for 2 days in DMEM mixed with 10% FBS, 50 nM IBMX, 1 µM DEX, and 10 µg/mL insulin. Two days after the initiation of the differentiation induction, the medium was replaced with DMEM mixed with 10% FBS and 10 µg/mL insulin. Two days after the replacement, the medium was replaced, and the cells were cultured until four days thereafter. Each *Cirsium brevicaule* A. Gray extract obtained as described above was added to the medium from the initiation of the induction of the (Results)

Figure 2:
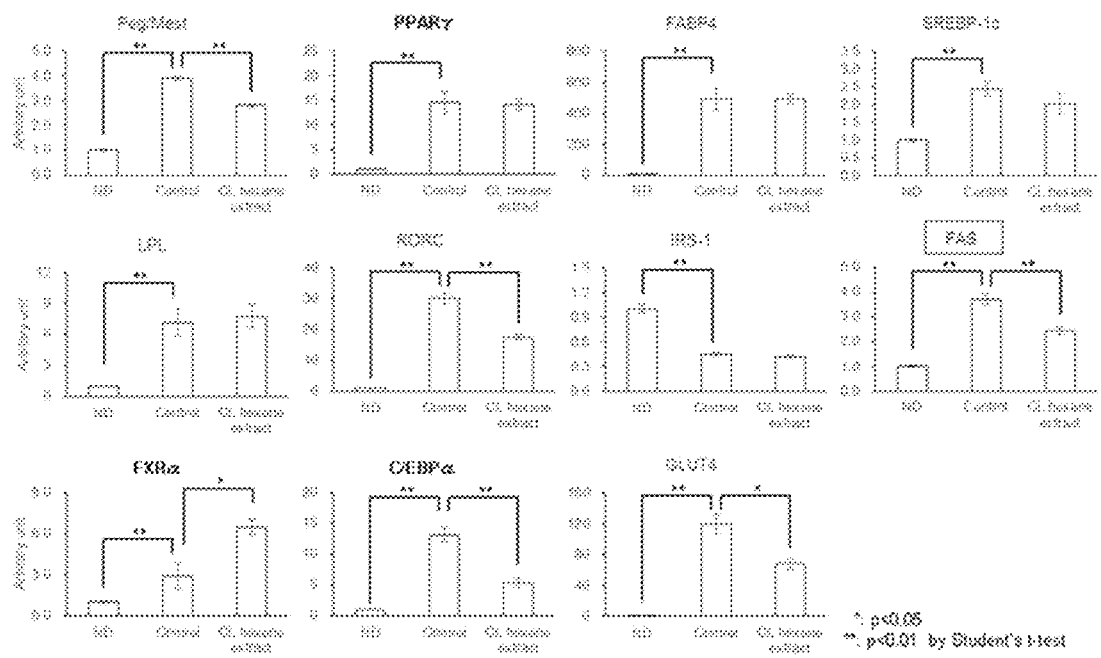
FIG. 2 is a view showing the influence of a *Cirsium brevicaule* A. Gray extract according to the present example on the expression of the lipolysis promotion-related genes and lipogenesis-related genes of cultured cells.

The results are shown in FIG. 2. In FIG. 2, "ND" and "CONTROL" are similar to those in FIG. 1. The expression of a fatty acid synthase (FAS) in the cells obtained by adding the hexane extract of the *Cirsium brevicaule* A. Gray leaf to the cells and culturing the cells was significantly reduced compared to the control.

Based on the above, it was suggested that the *Cirsium brevicaule* A. Gray extract according to the present example reduced the expression of the fatty acid synthase (FAS), to thereby inhibit the accumulation of fat in the fat cells.

Example 2

An animal experiment was conducted using the lyophilized powder of a *Cirsium brevicaule* A. Gray leaf.

57BL/6 mice (male) were purchased, and preliminary breeding of the mice was carried out for 1 week to acclimate the mice to a new environment. Then, the mice were divided into three groups each including six mice, and the mice in each group were fed with a feed (see Table 2) obtained by blending a high-fat food (basic composition of standard purified diet (AIN-76) for nutrition research using rodents, presented in 1977 by the American Institute of Nutrition (AIN), blended with 15% of corn oil) with 0%, 5%, or 10% of the lyophilized powder of a *Cirsium brevicaule* A. Gray leaf (similar to that in Example 1), and were bred for 4 weeks. During the breeding period, diet intakes were adjusted so that the intake energies of the mice in each group were equivalent to each other. In FIGS. 3 to 6, "Cntl (=control)" represents the group in which the mice were fed with a feed containing no lyophilized powder of the *Cirsium brevicaule* A. Gray leaf (that is, group of "0%" in Table 2).

TABLE 2

Composition of Experimental Feed (Feed in g/kg)

|  | 0% | 5% (g) | 10% |
|---|---|---|---|
| Lipid (corn oil) | 150 | 147.35 | 144.7 |
| Protein (milk casein) | 200 | 190.45 | 180.9 |
| Carbohydrate (corn starch) | 150 | 143.65 | 137.3 |
| Carbohydrate (sucrose) | 394.8 | 384.85 | 374.9 |
| Dietary fiber (cellulose) | 50 | 31.1 | 12.2 |
| Vitamins (AIN-76 vitamin mix) | 35 | 35 | 35 |
| Minerals (AIN-76 mineral mix) | 10 | 10 | 10 |
| DL-methionine | 3 | 3 | 3 |
| Choline tartrate | 2 | 2 | 2 |
| Water | 0 | 5.2 | 2.6 |
| *Cirsium brevicaule* A. Gray leaf powder* | 0 | 50 | 100 |
| Total | 1000 | 1000 | 1000 |

After the end of the breeding, each tissue and blood of the mice were collected to measure the body and organ weights (FIG. 3), tissue weights (FIG. 4), blood parameters (FIG. 5), and various hepatic parameters (FIG. 6) of the mice in each group. As a testing method, the Dunnett method as a multiple testing procedure was used to detect the significant difference between a control group and an experimental group.

The various parameters of the mice were measured using the following commercially available kits:

Neutral fat (FIG. 5): Triglyceride E-test WAKO (Wako Pure Chemical Industries, Ltd.);
Total cholesterol (FIG. 5): Cholesterol E-test WAKO (Wako Pure Chemical Industries, Ltd.);
Free fatty acid (FIG. 5): NEFA C-test WAKO (Wako Pure Chemical Industries, Ltd. Co., Ltd.);
Insulin (FIG. 5): Mouse Insulin ELISA Kit (Morinaga Institute of Biological Science, Inc. Co., Ltd.); and
Hepatic disorder markers (ALT and AST) (FIG. 6): Transaminase CII-test WAKO (Wako Pure Chemical Industries, Ltd.).

The liver neutral fat and liver total cholesterol levels of the mice (FIG. 6) were measured as follows. The livers were harvested from the bred mice, and the lipids of the livers were extracted using the method of Mr. Folch (Folch J, Lees M and Sloane Stanley G H, A simple method for the isolation and purification of total lipides from animal tissues; The Journal of Biological Chemistry 1957; 226 (1): 497-509). The extracted lipids of each liver were dissolved in isopropanol containing 10% of Triton X-100 to make a lipid extraction liquid. The neutral fat level in the lipid extraction liquid was measured using the method of Mr. Fletcher (Fletcher M J, A colorimetric method for estimating serum triglycerides; Clinica Chimica Acta 1968; 22 (3): 393-397). Further, the total cholesterol level in the lipid extraction liquid was measured using Cholesterol E-test WAKO (Wako Pure Chemical Industries, Ltd.).

(Results)

Figure 3:
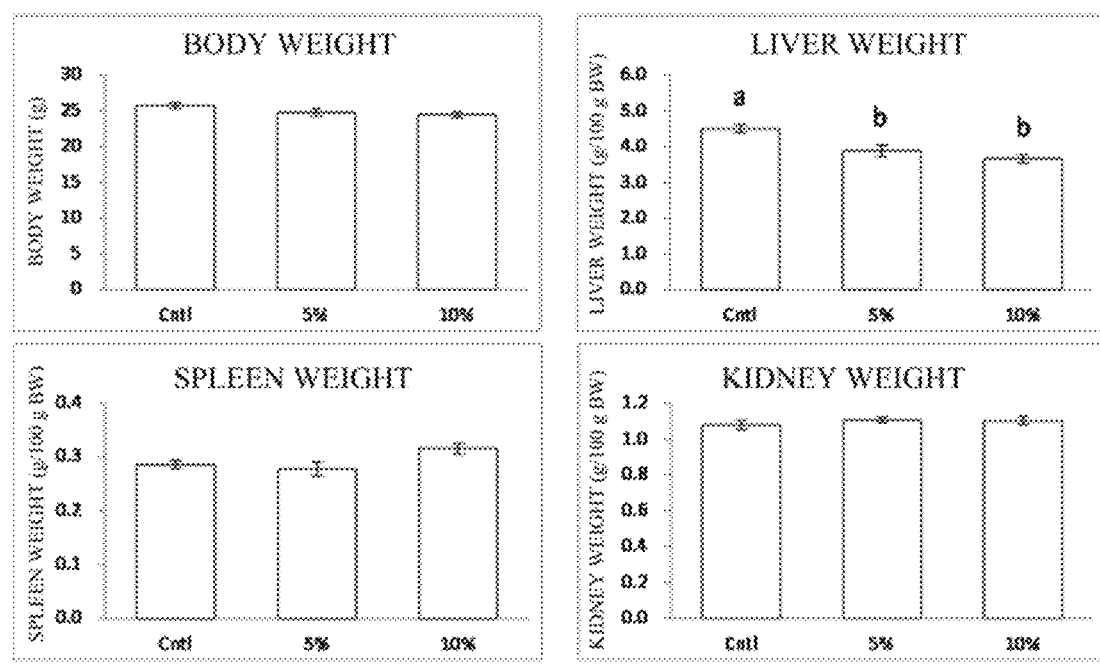
FIG. 3 is a view showing the influence of the lyophilized powder of *Cirsium brevicaule* A. Gray leaf according to the present example on the body weight, liver weight, spleen weight, and kidney weight of mice fed with a high-fat diet.

FIG. 3 shows the measurement results of the body, liver, spleen, and kidney weights. No variations were seen in the body, spleen, and kidney weights, while the liver weight was significantly decreased with increasing the content of *Cirsium brevicaule* A. Gray leaf in the feed.

Figure 4:
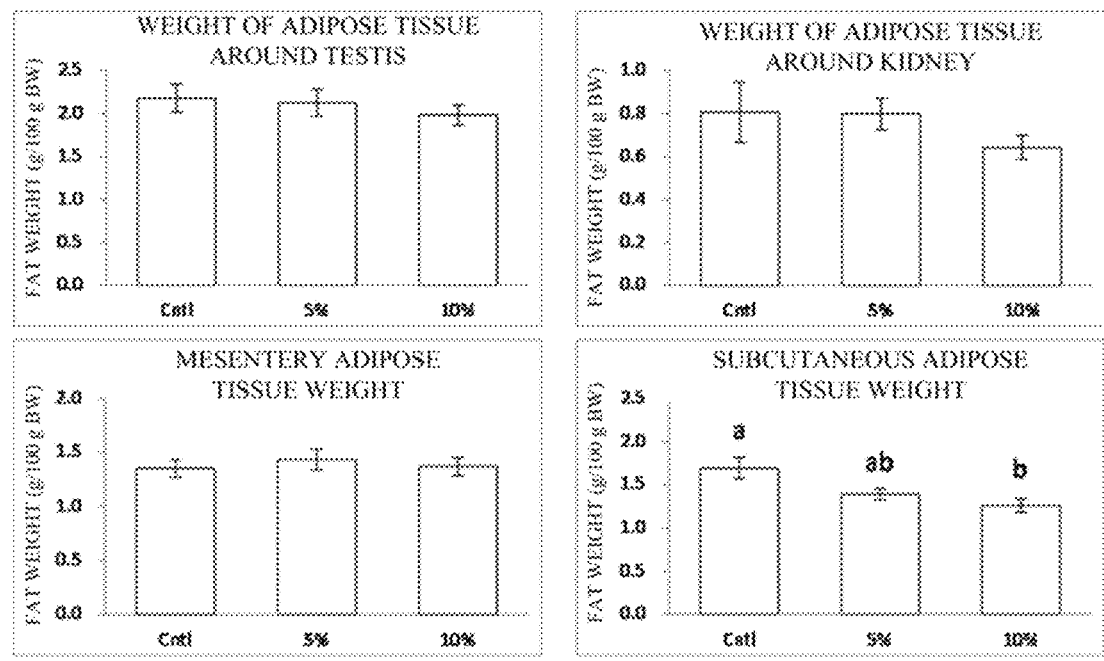
FIG. 4 is a view showing the influence of the lyophilized powder of *Cirsium brevicaule* A. Gray leaf according to the present example on the weight of the adipose tissue around the testis, the weight of the adipose tissue around the kidney, the weight of the mesentery adipose tissue, and the weight of the subcutaneous adipose tissue of mice fed with a high-fat diet.

FIG. 4 shows the measurement results of the weight of the adipose tissue around the testis, the weight of the adipose tissue around the kidney, the weight of the mesentery adipose tissue, and the weight of the subcutaneous adipose tissue. No variations were seen in the weight of the adipose tissue around the testis, the weight of the adipose tissue around the kidney, and the weight of the mesentery adipose tissue, while the weight of the subcutaneous adipose tissue was significantly decreased with increasing the content of *Cirsium brevicaule* A. Gray leaf in the feed.

Figure 5:
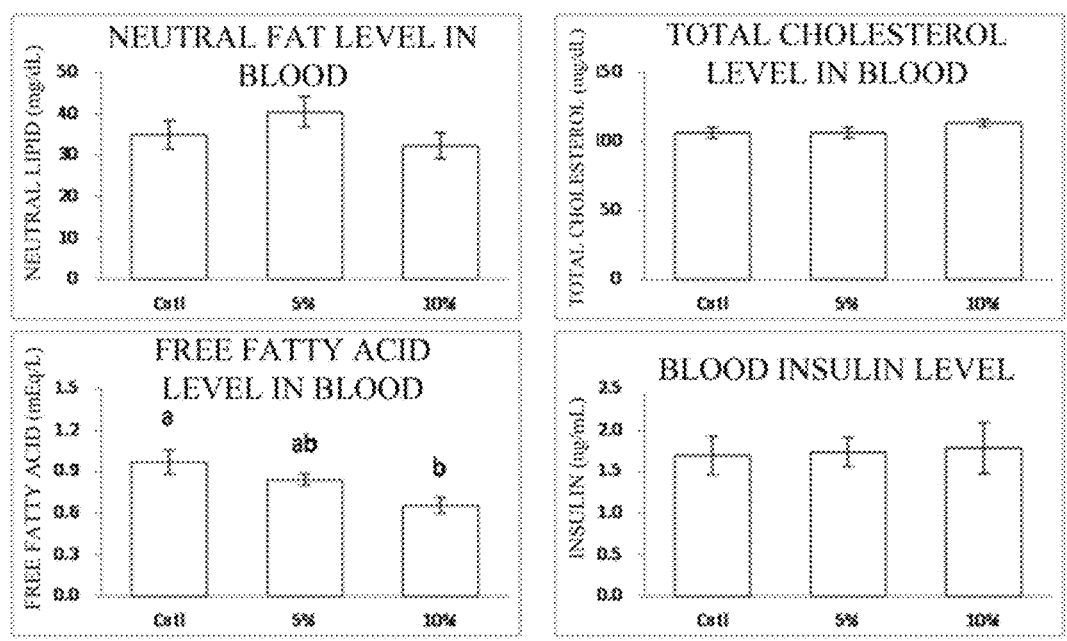
FIG. 5 is a view showing the influence of the lyophilized powder of *Cirsium brevicaule* A. Gray leaf according to the present example on the neutral fat level in blood, total cholesterol level in blood, free fatty acid level in blood, and blood insulin level of mice fed with a high-fat diet.

FIG. 5 shows the measurement results of the neutral fat level in blood, the total cholesterol level in blood, the free fatty acid level in blood, and the blood insulin level. No variations were seen in the neutral fat level in blood, the total cholesterol level in blood, and the blood insulin level, while the free fatty acid level in blood was significantly decreased with increasing the content of *Cirsium brevicaule* A. Gray leaf in the feed.

Figure 6:
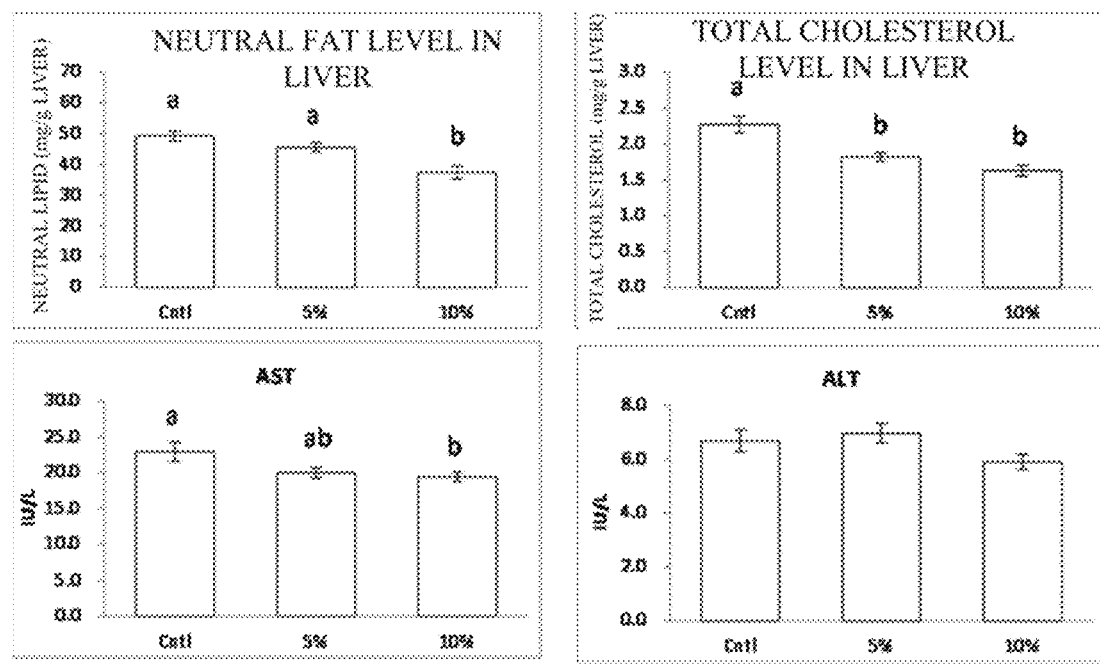
FIG. 6 is a view showing the influence of the lyophilized powder of *Cirsium brevicaule* A. Gray leaf according to the present example on the neutral fat level in the liver, total cholesterol level in the liver, and blood markers (AST and ALT) of hepatic disorders of mice fed with a high-fat diet.

FIG. 6 shows the measurement results of the neutral fat level in the liver, the total cholesterol level in the liver, and the blood markers (AST and ALT) of hepatic disorders. Not only the neutral fat level in the liver and the total cholesterol level in the liver but also the blood markers (AST and ALT) of hepatic disorders were significantly decreased.

(Influence on Expression of Lipolysis Promotion-Related Genes and Lipogenesis-Related Genes)

The influence of the intake of a *Cirsium brevicaule* A. Gray leaf on the expression of the lipolysis promotion-related genes and lipogenesis-related genes (Table 3) of the fat cells and livers of mice fed with a high-fat diet was examined.

To 0.1 g of adipose tissue and 0.1 g of liver collected from the bred mice described above, 800 μL of TRIzol reagent (Ambion) was added, and the tissue was lysed by a homogenizer. The cell lysate was mixed with 200 μL of chloroform and left standing at room temperature for 5 minutes, followed by separating the cell lysate into two layers by centrifugation at 12,000×g for 15 minutes. The collected upper layer (water layer) was mixed with an equivalent amount of 70% ethanol, to purify total RNA using Pure Link RNA Mini Kit (Ambion). Using High Capacity RNA-to-cDNA Kit (Applied Biosystems), cDNA was synthesized from 2 μg of total RNA.

Fast SYBR Green Master Mix (Applied Biosystems) and a primer for sensing gene expression of interest (Table 3) were added to the synthesized cDNA as a template, and gene expression analysis was carried out by StepOne Real-Time PCR System (Applied Biosystems). Each gene expression data was corrected using the level of 18S rRNA as an internal standard for the liver and the expression level of ACTB as an internal standard for the adipose tissue, and the expression of the lipolysis promotion-related genes and lipogenesis-related genes (Table 3) of each tissue due to the intake of *Cirsium brevicaule* A. Gray was analyzed.

TABLE 3

| Gene name | | Forward primer | Reverse primer |
|---|---|---|---|
| ACTB (internal standard) | — | SEQ ID NO: 1 | SEQ ID NO: 2 |
| 18S rRNA (internal standard) | — | SEQ ID NO: 25 | SEQ ID NO: 26 |
| FAS | Fatty acid synthase (FAS) | SEQ ID NO: 17 | SEQ ID NO: 18 |
| C/EBP α | CCAAT-enhancer-binding proteins α | SEQ ID NO: 21 | SEQ ID NO: 22 |
| PPAR α | Peroxisome Proliferator-Activated Receptor α | SEQ ID NO: 27 | SEQ ID NO: 28 |
| PPAR γ | Peroxisome Proliferator-Activated Receptor γ | SEQ ID NO: 5 | SEQ ID NO: 6 |
| SREBP-1c | Sterol regulatory element-binding protein-1c | SEQ ID NO: 9 | SEQ ID NO: 10 |
| CPT1b | Carnitine palmitoyltransferase 1b | SEQ ID NO: 29 | SEQ ID NO: 30 |
| CPT1a | Carnitine palmitoyltransferase 1a | SEQ ID NO: 31 | SEQ ID NO: 32 |

(Results)

Figure 7:
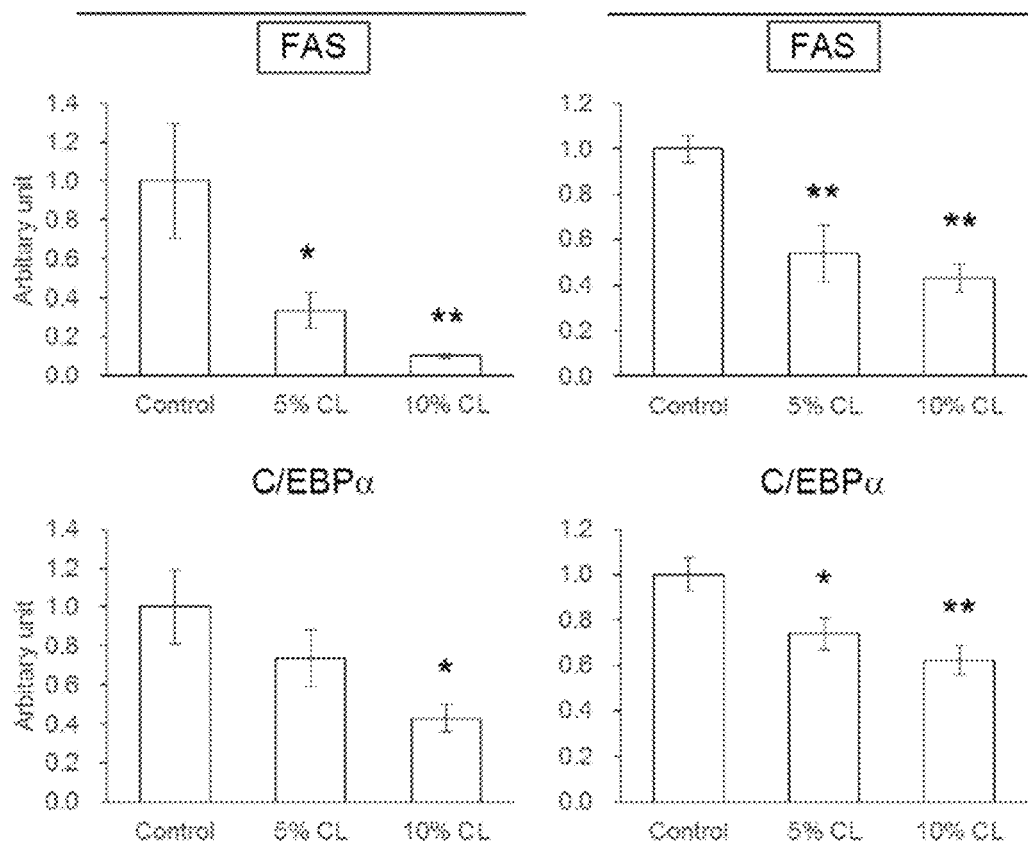
FIG. 7 is a graphical view showing the influence of the lyophilized powder of *Cirsium brevicaule* A. Gray leaf according to the present example on the expression of the lipolysis promotion-related genes and lipogenesis-related genes in the subcutaneous white adipose tissue and white adipose tissue around the kidney of mice fed with a high-fat diet.
Figure 8:
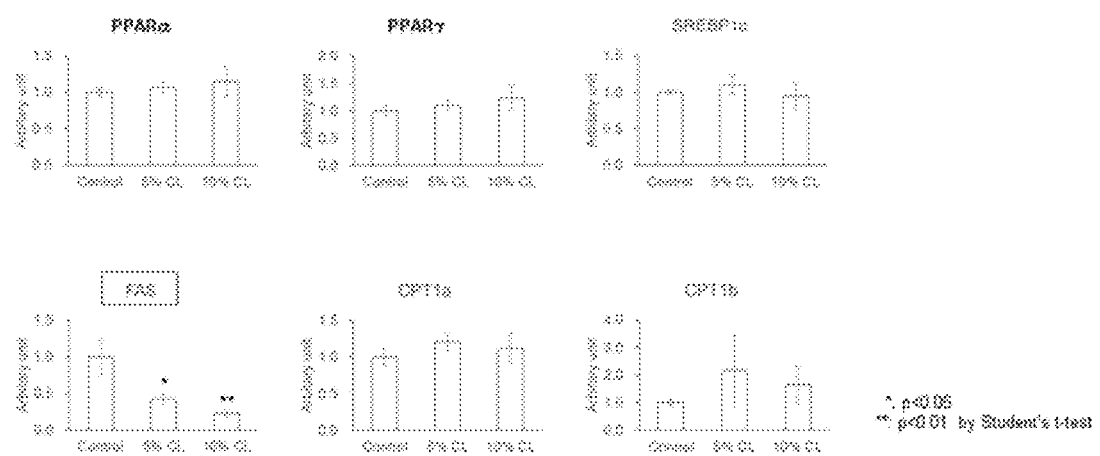
FIG. 8 is a graphical view showing the influence of the lyophilized powder of *Cirsium brevicaule* A. Gray leaf according to the present example on the expression of the lipolysis promotion-related genes and lipogenesis-related genes in the liver of mice fed with a high-fat diet.

FIG. 7 shows the results in the subcutaneous white adipose tissue and the white adipose tissue around the kidney, and FIG. 8 shows the results in the liver. Like FIGS. 3 to 6, "CONTROL" in FIG. 7 and FIG. 8 represents the group in which the mice were fed with a feed containing no lyophilized powder of the *Cirsium brevicaule* A. Gray leaf (that is, group of "0%" in Table 2). In the mice fed with a high-fat diet, taking the *Cirsium brevicaule* A. Gray leaf, the expression of a fatty acid synthase (FAS) in the subcutaneous white adipose tissue and the white adipose tissue around the kidney was dose-dependently reduced (FIG. 7), and the expression of FAS in the liver was also dose-dependently reduced (FIG. 8).

Based on the above, it was suggested that the intake of the lyophilized powder of the *Cirsium brevicaule* A. Gray leaf according to the present example resulted in a reduction in the expression of FAS, to thereby inhibit the accumulation of fat in the fat cells and the liver.

Example 3

The fat accumulation inhibitory effects of hexane and chloroform extracts obtained from a *Cirsium brevicaule* A. Gray leaf were investigated in detail.

(Preparation of Hexane Extract)

Figure 9:
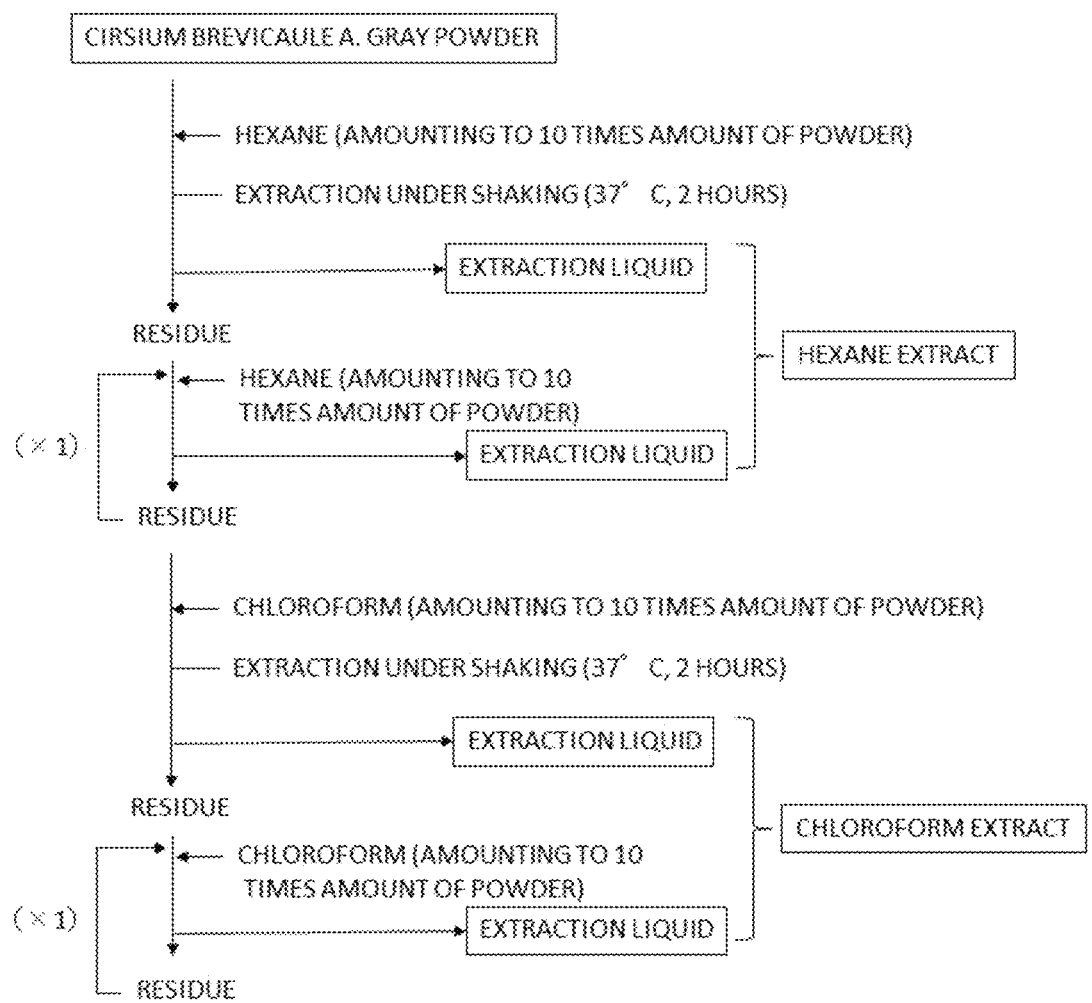
FIG. 9 is a view for explaining the steps of obtaining a hexane extract and a chloroform extract from *Cirsium brevicaule* A. Gray.

The lyophilized powder of a *Cirsium brevicaule* A. Gray leaf was obtained in the same manner as in Example 1. Extraction treatment was carried out by adding hexane amounting to 10 times the amount of the lyophilized powder to the lyophilized powder and by immersing the lyophilized powder in the hexane under shaking at 37° C. for 2 hours. After the extraction, an extraction liquid was separated by filtration under reduced pressure, and the residue was washed twice with hexane amounting to 10 times the amount of the lyophilized powder. The liquid generated by the washing was mixed into the extraction liquid obtained in advance, to make a hexane extract (FIG. 9).

(Preparation of Chloroform Extract)

The residue obtained after the washing with the hexane in advance was allowed to be under reduced pressure, to thereby remove the remaining hexane. Extraction treatment was carried out by adding chloroform amounting to 10 times the amount of the lyophilized powder to the residue obtained after the removal of the hexane and by immersing the residue in the chloroform under shaking at 37° C. for 2 hours. After the extraction, an extraction liquid was separated by filtration under reduced pressure, and the residue was washed twice with chloroform amounting to 10 times the amount of the lyophilized powder. The liquid generated by the washing was mixed into the extraction liquid obtained in advance, to make a chloroform extract (FIG. 9).

(Investigation of Fat Accumulation Inhibitory Effect of Hexane Extract)

Figure 10:
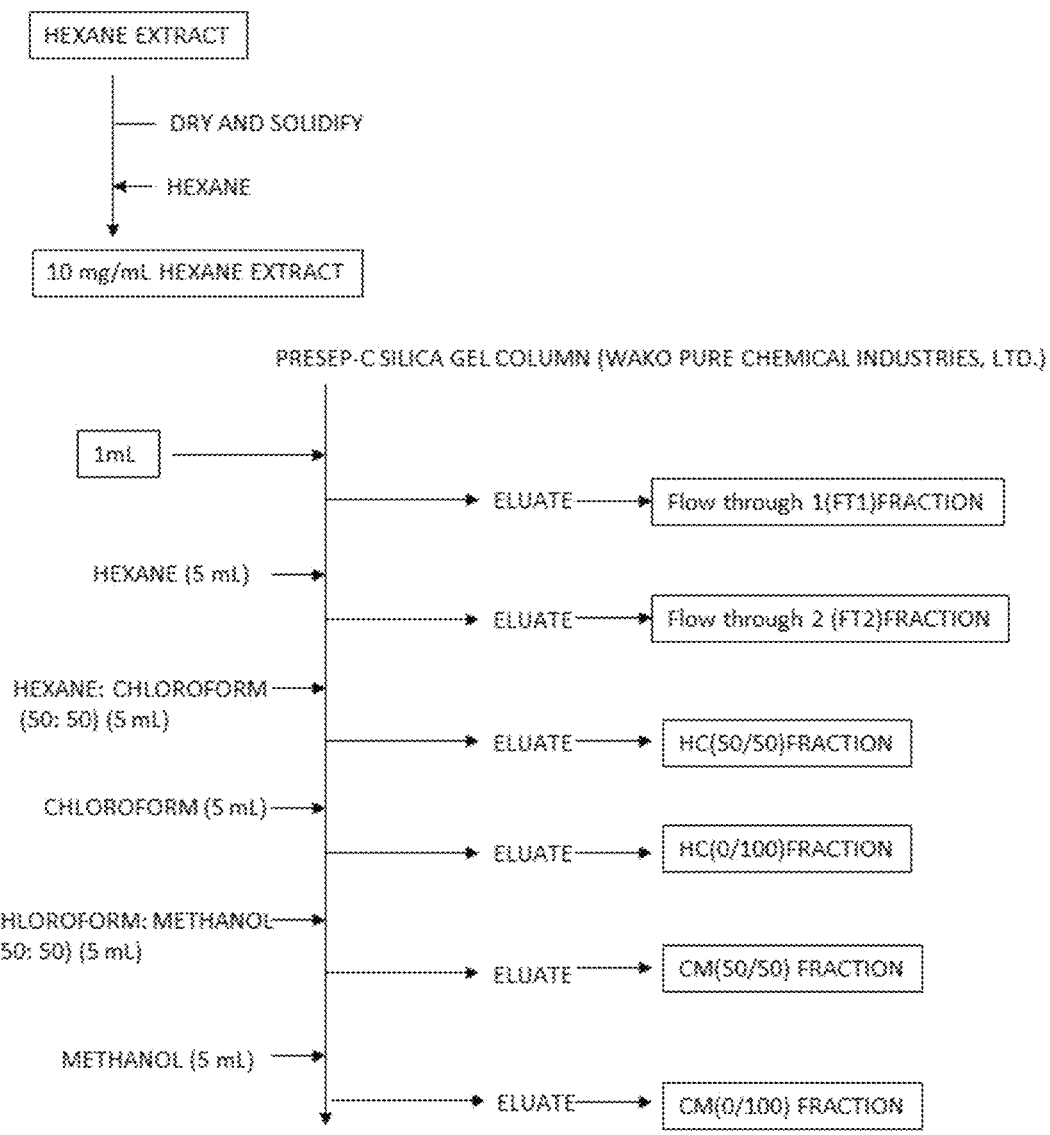
FIG. 10 is a view for explaining the step of obtaining each fraction from the hexane extract.

The hexane extract obtained by the above preparation method was dried and solidified under reduced pressure, and was dissolved in hexane, to obtain 10 mg/mL of hexane extract solution (FIG. 10).

The above-described hexane extract solution was subjected to solid phase extraction using Presep-C Silica Gel Column (Wako Pure Chemical Industries, Ltd.), to thereby obtain each fraction. More specifically, 1 mL of the above-described hexane extract solution was applied to Presep-C Silica Gel Column, to obtain an eluate as "FT1 fraction", as shown in FIG. 10. Then, 5 mL of hexane was allowed to flow to obtain an eluate as "FT2 fraction". Then, 5 mL of hexane:chloroform (50:50) was allowed to flow to obtain an eluate as "HC (50/50) fraction". Then, 5 mL of chloroform was allowed to flow to obtain an eluate as "HC (0/100) fraction". Then, 5 mL of chloroform:methanol (50:50) was allowed to flow to obtain an eluate as "CM (50/50) fraction". Then, 5 mL of methanol was allowed to flow to obtain an eluate as "CM (0/100) fraction". Each fraction was dried and solidified, and then dissolved in 1 mL of dimethyl sulfoxide.

The influence of each fraction on accumulation of neutral fat in 3T3-L1 cells was evaluated. The culture of the 3T3-L1 cells and the induction of the differentiation of the 3T3-L1 cells into fat cells were carried out in the same manner as in Example 1. From the initiation of the induction of the differentiation of the 3T3-L1 cells to the end of the experiment, a medium to which each fraction dissolved in 1 mL of dimethyl sulfoxide as described above was added to be 0.5% (v/v) was used. Cultured fat cells obtained by adding each fraction to the cells and culturing the cells were lysed, lipids were extracted from the cell lysate, and an intracellular neutral fat level was measured. The lysis of the cultured fat cells, the extraction of the lipids, and the measurement of the intracellular neutral fat level were carried out in the same manner as in Example 1.

(Results)

Figure 11:
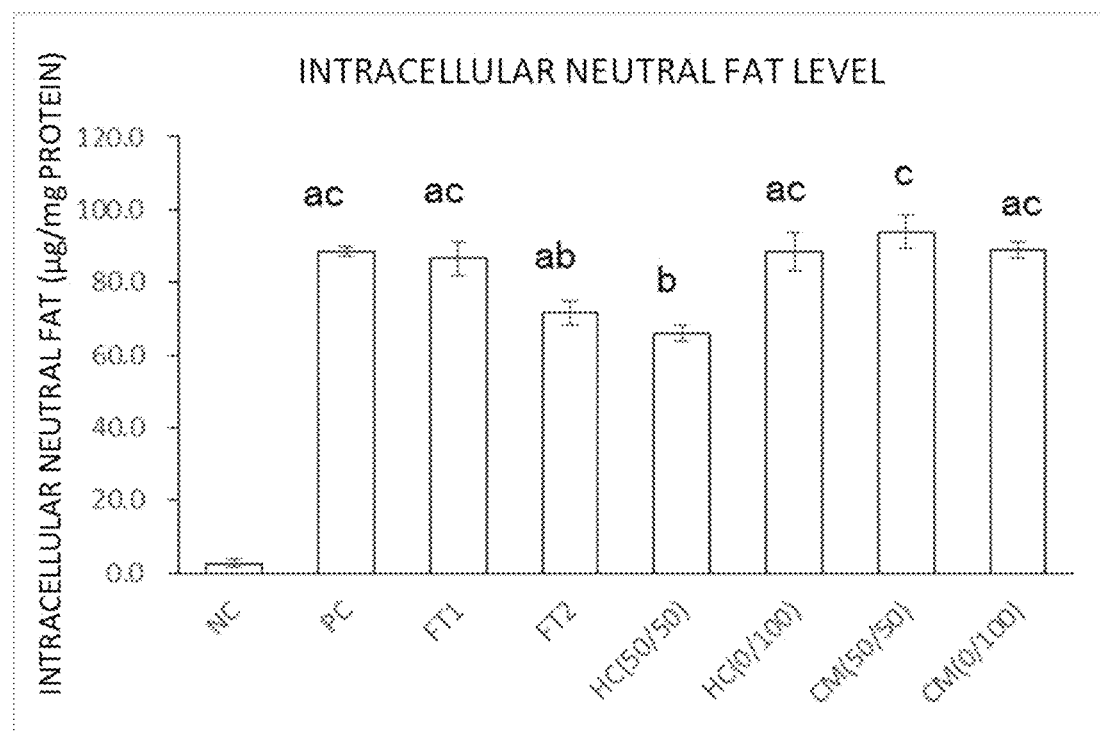
FIG. 11 is a view showing the results of measurement of an intracellular neutral fat level in each fraction of the hexane extract according to the present example.

The results of the measurement of the intracellular neutral fat level are shown in FIG. 11. In FIG. 11, "NC" shows 3T3-L1 cells subjected to no differentiation induction treatment, and "PC" shows cells obtained by subjecting the cells to differentiation induction treatment, adding dimethyl sulfoxide to the cells, and culturing the cells. It was shown that an intracellular neutral fat level in cells obtained by adding the HC (50/50) fraction to the cells and culturing the cells was significantly lower than that in "PC" (FIG. 11).

Based on the above, it was shown that the hexane extract of the *Cirsium brevicaule* A. Gray leaf according to the present example inhibited lipid accumulation. In particular, it was shown that the HC (50/50) fraction in the hexane extract had an excellent lipid accumulation inhibitory effect.

(Investigation of Influence of Chloroform Extract on Expression of Lipogenesis-Related Genes)

Figure 12:
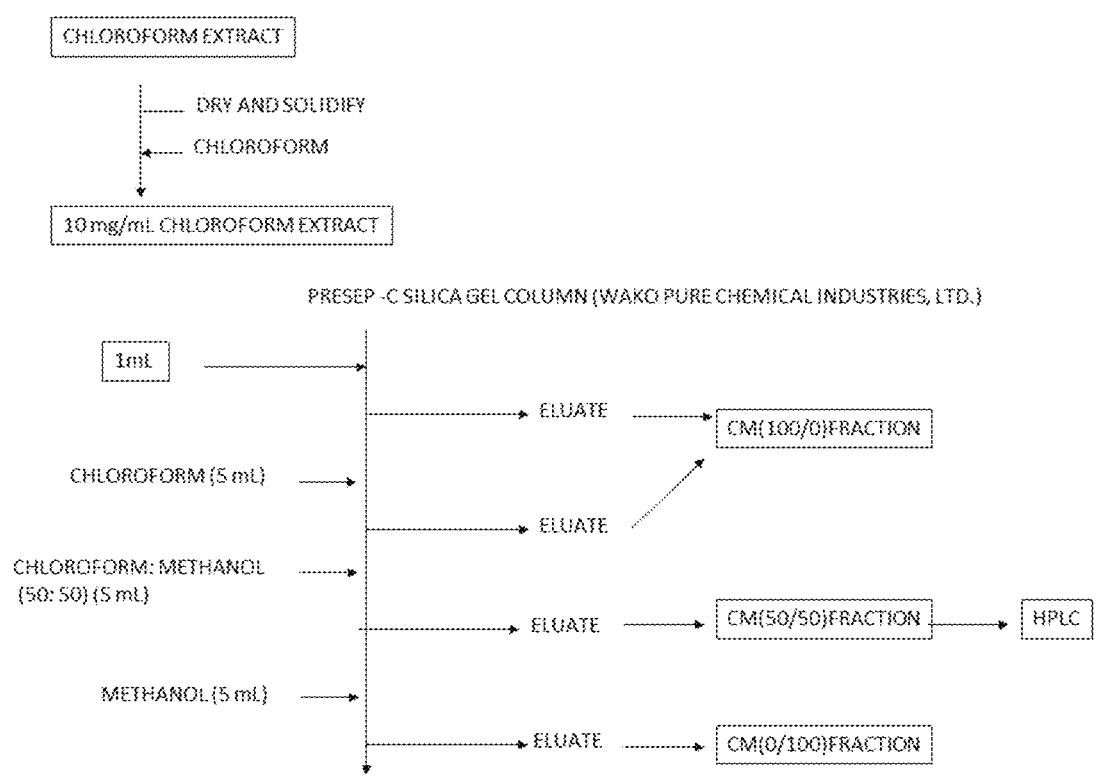
FIG. 12 is a view for explaining the step of obtaining each fraction from the chloroform extract.

The chloroform extract obtained by the above-described preparation method was dried and solidified under reduced pressure, and was dissolved in chloroform, to obtain 100 mg/mL of chloroform extract solution (FIG. 12).

The above-described chloroform extract solution was subjected to solid phase extraction using Presep-C Silica Gel Column (Wako Pure Chemical Industries, Ltd.), to thereby obtain each fraction. More specifically, an eluate obtained by applying 1 mL of the above-described hexane extract solution to Presep-C Silica Gel Column and an eluate obtained by then allowing 5 mL of chloroform to flow were mixed with each other, to obtain the resultant as "CM (100/0) fraction", as shown in FIG. 12. Then, 5 mL of chloroform:methanol (50:50) was allowed to flow to obtain an eluate as "CM (50/50) fraction". Then, 5 mL of methanol was allowed to flow to obtain an eluate as "CM (0/100) fraction". Each fraction was dried and solidified, and then dissolved in 1 mL of dimethyl sulfoxide.

The influence of each fraction on the expression of lipogenesis-related genes (FAS) was evaluated using HepG2 cells as human liver cancer cells. The culture of the cells and the induction of differentiation into fat cells were carried out in the same manner as in Example 1 except that the HepG2 cells were used instead of the 3T3-L1 cells. From the initiation of the induction of the differentiation of the HepG2 cells to the end of the experiment, a medium to which each fraction dissolved in 1 mL of dimethyl sulfoxide as described above was added to be 0.5% (v/v) was used. The purification of total RNA from the cells, the synthesis of cDNA, and a real-time PCR method were carried out in the same manner as in Example 1, and the following primers for sensing FAS expression were used:

```
                                          (SEQ ID NO: 33)
FAS-sense:            TCGTGGGCTACAGCATGGT;

(SEQ ID NO: 34)
FAS-anti-sense:       GCCCTCTGAAGTCGAAGAAG;

(SEQ ID NO: 35)
ACTB-sense:           TCACCGAGCGCGGCT;
and (SEQ ID NO: 36)
ACTB-anti-sense:      TAATGTCACGCACGATTTCCC.
```

Each gene expression data was corrected with the expression level of housekeeping gene ((3-actin, ACTB) as an internal standard, to evaluate the mRNA level of lipogenesis-related genes (FAS) in the cells treated with each fraction.

Figure 13:
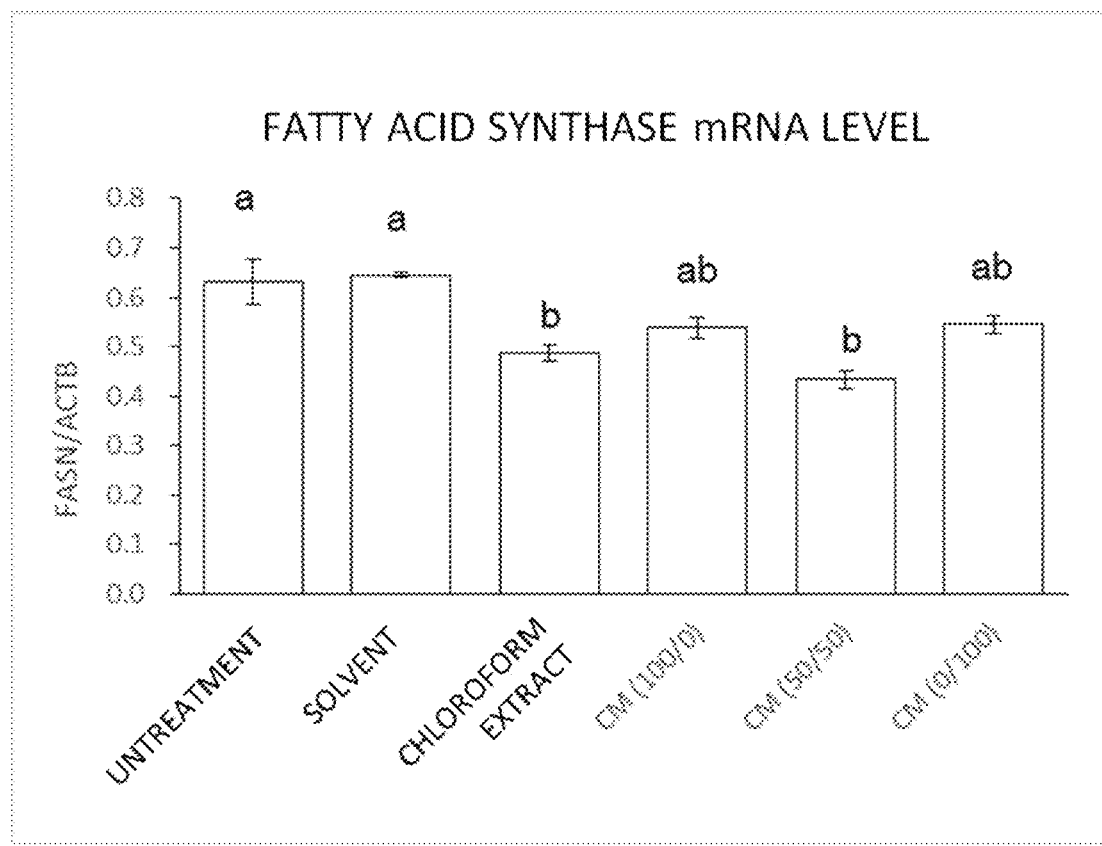
FIG. 13 is a view showing the results of measurement of a fatty acid synthase mRNA level in each fraction of the chloroform extract according to the present example.

The results are shown in FIG. 13. In FIG. 13, "UNTREATMENT" shows cells to which no dimethyl sulfoxide was added, and "SOLVENT" shows cells obtained by adding dimethyl sulfoxide to the cells and culturing the cells. The expression of a fatty acid synthase (FAS) in cells obtained by adding the chloroform extract and the CM (50/50) fraction to the cells and culturing the cells was significantly reduced compared to "UNTREATMENT" and "SOLVENT".

Figure 14:
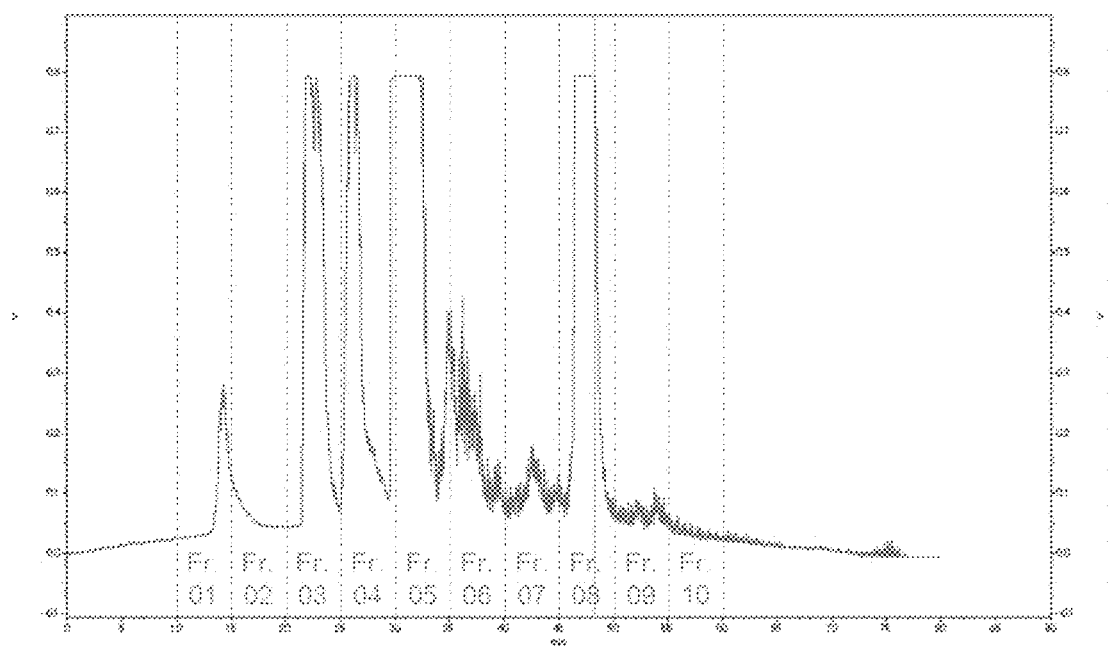
FIG. 14 is a view showing Fractions obtained from the CM (50/50) fraction of the chloroform extract according to the present example.

In order to investigate, in more detail, the CM (50/50) fraction showing the reduction in the expression of the fatty acid synthase (FAS), the CM (50/50) fraction was subjected to HPLC (described later) and fractionated into Fractions 1 to 10 (Frs. 01 to 10) (FIG. 14).

An HPLC technique will be specifically described. An instrument manufactured by SHIMADZU CORPORATION was used as an HPLC instrument, and Evaporative Light Scattering Detector (ELSD-LT, SHIMADZU CORPORATION) was used as a detector. A column used was a silica gel column: Develosil Packed Column (60-3 8.0/250 (NM), Nomura Chemical Co., Ltd.), and gradient analysis (flow rate of 0.5 mL/min) was carried out using chloroform and methanol. Gradient conditions are as follows:

0:00 Start ($CHCl_3$:MeOH=100:0);
60:00 ($CHCl_3$:MeOH=75:15);
70:00 ($CHCl_3$:MeOH=50:50); and
90:00 stop ($CHCl_3$:MeOH=50:0).

The influence of each of Fractions 1 to 10 (Frs. 01 to 10) obtained by HPLC on the expression of lipogenesis-related genes (FAS) was evaluated using HepG2 in the same manner as described above.

Figure 15:
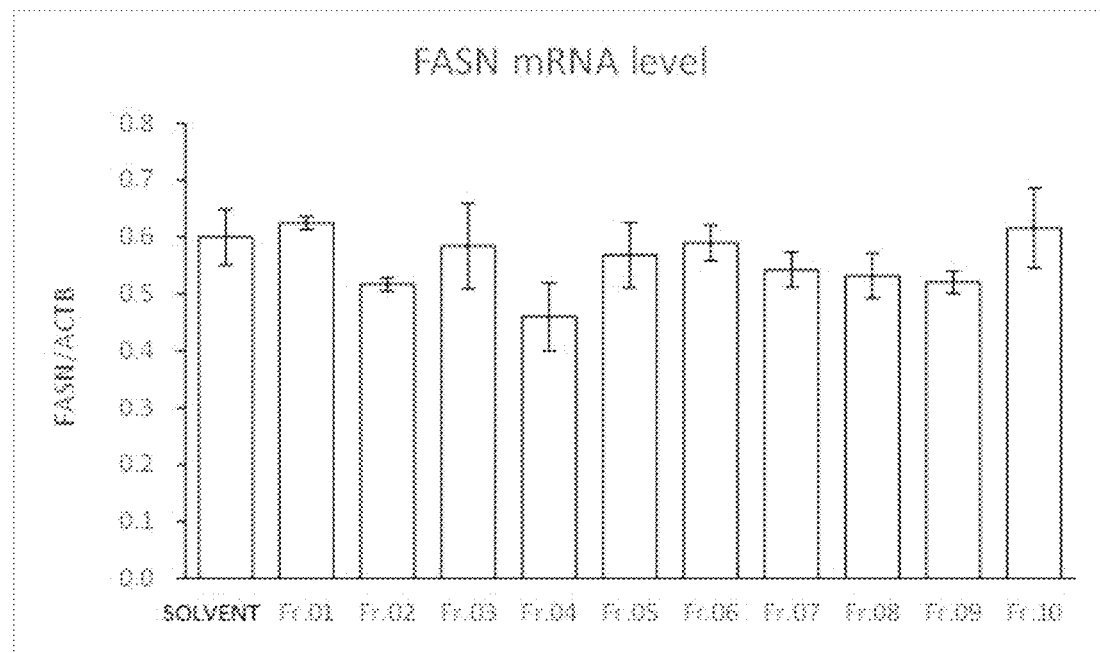
FIG. 15 is a view showing the results of measurement of a fatty acid synthase mRNA level in each Fraction.

The results are shown in FIG. 15. In FIG. 15, "SOLVENT" shows cells obtained by adding dimethyl sulfoxide to the cells and culturing the cells. Cells obtained by adding Fraction 4 (Fr. 04) to the cells and culturing the cells showed the lowest expression of a fatty acid synthase (FAS).

In order to investigate, in more detail, Fraction 4 (Fr. 04) showing the lowest expression of the fatty acid synthase (FAS), the mRNA level of lipogenesis-related genes (FAS) was evaluated using HepG2 in the same manner as described above.

Figure 16:
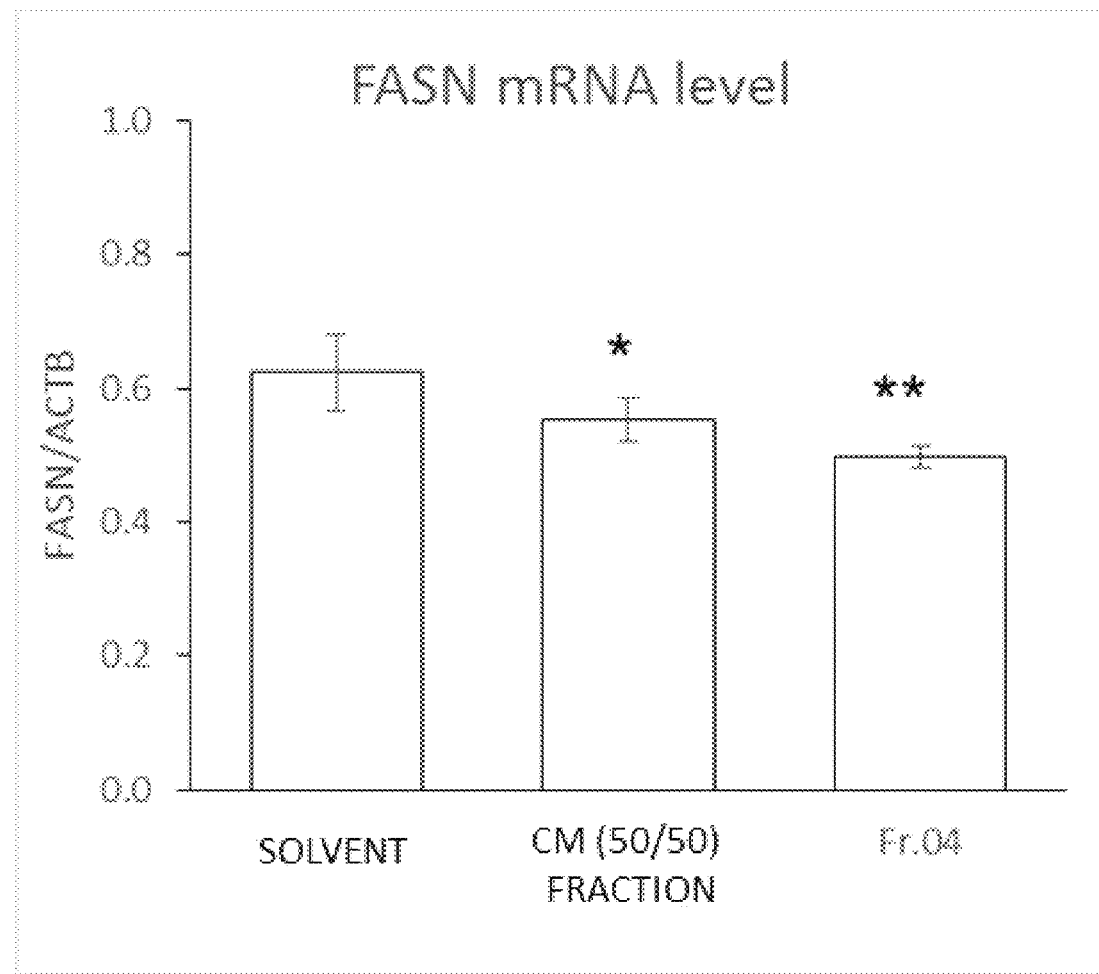
FIG. 16 is a view showing the results of measurement of a fatty acid synthase mRNA level in Fraction 4.

The results are shown in FIG. 16. In FIG. 16, "SOLVENT" shows cells obtained by adding dimethyl sulfoxide to the cells and culturing the cells, and "CM (50/50) FRACTION" shows cells obtained by adding the CM (50/50) fraction described above and culturing the cells. The expression of the fatty acid synthase (FAS) in "Fr. 04" was significantly reduced compared to "SOLVENT", and the reduction in the expression of the fatty acid synthase (FAS) in "Fr. 04" was greater than that in "CM (50/50) FRACTION".

Based on the above, it was suggested that the chloroform extract of the *Cirsium brevicaule* A. Gray leaf according to the present example resulted in a reduction in the expression of the fatty acid synthase (FAS). It was shown that in particular, the CM (50/50) fraction in the chloroform extract, and, in addition, Fraction 4 (Fr. 04) in the CM (50/50) fraction had the excellent effect of reducing the expression of a fatty acid synthase (FAS).

Based on the above, it was shown that the *Cirsium brevicaule* A. Gray extract according to the present example had the effect of inhibiting lipid accumulation and reducing the expression of a fatty acid synthase (FAS).

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

We claim:

1. A method of treating fatty liver comprising administering an effective amount of *Cirsium brevicaule* A. Gray, which is a plant belonging to a genus *Cirsium*, to a patient in need of the treatment.

2. The method of claim 1, wherein the *Cirsium brevicaule* A. Gray is in a form of an extract that is obtained by extracting the *Cirsium brevicaule* A. Gray with a solvent.

3. The method of claim 1, wherein the *Cirsium brevicaule* A. Gray is in a form of powder.

* * * * *